(12) United States Patent
Jollez et al.

(10) Patent No.: US 11,013,823 B2
(45) Date of Patent: May 25, 2021

(54) WATER-ABSORBING MATERIAL AND USES THEREOF

(71) Applicant: 7905122 Canada Inc., Boucherville (CA)

(72) Inventors: Paul Jollez, Sherbrooke (CA); Isabelle Bolduc, Saint-Hubert (CA); Stéphane Chevigny, Boucherville (CA); Olivier Sigouin, St-Bruno-de-Montarville (CA)

(73) Assignee: 7905122 CANADA INC., Quebec (CA)

( * ) Notice: Subject to any disclaimer, the term of this patent is extended or adjusted under 35 U.S.C. 154(b) by 319 days.

(21) Appl. No.: 16/090,366

(22) PCT Filed: Sep. 1, 2016

(86) PCT No.: PCT/CA2016/051037
§ 371 (c)(1),
(2) Date: Oct. 1, 2018

(87) PCT Pub. No.: WO2017/165953
PCT Pub. Date: Oct. 5, 2017

(65) Prior Publication Data
US 2019/0117823 A1 Apr. 25, 2019

Related U.S. Application Data

(60) Provisional application No. 62/316,639, filed on Apr. 1, 2016.

(51) Int. Cl.
*A61L 15/56* (2006.01)
*B01J 20/24* (2006.01)
(Continued)

(52) U.S. Cl.
CPC ............ *A61L 15/56* (2013.01); *A01K 1/0155* (2013.01); *A01K 1/0157* (2013.01); *A61L 15/60* (2013.01);
(Continued)

(58) Field of Classification Search
CPC ....... A61L 15/56; A61L 15/60; A61K 1/0155; A61K 1/0157; B01J 20/24; B01J 20/261;
(Continued)

(56) References Cited

U.S. PATENT DOCUMENTS 4,460,684 A 7/1984 Bauer
4,615,923 A 10/1986 Marx
(Continued)

FOREIGN PATENT DOCUMENTS

CA 2308537 11/2000
CA 2352502 1/2002
(Continued)

OTHER PUBLICATIONS

International Search Report and Written Opinion for PCT/CA2016051037, dated Nov. 16, 2016.

*Primary Examiner* — Robert J Eom
(74) *Attorney, Agent, or Firm* — Avant Law Group, LLC

(57) ABSTRACT

A chromogenic absorbent material for detecting a detectable substance in a water-containing medium, such as animal urine, is provided. The detectable substance may be indicative of a disease or condition, and the water-containing medium may be an excretion, blood, plasma, an aqueous solution or a solid impregnated with an aqueous solution. The chromogenic absorbent material may include a trigger agent, a chromogenic indicator convertible into a chromogenically active substance in the presence of the trigger agent and the detectable substance, and an absorptive material which is porous, for absorbing the water-containing medium. The absorptive material may include a water-absorbing polysaccharide providing absorptive properties to the chromogenic absorbent material. The trigger agent, the chromogenic indicator and the detectable substance are preferably unreactive to the absorptive material.

20 Claims, 16 Drawing Sheets

(51) Int. Cl.
  *B01J 20/26* (2006.01)
  *B01J 20/28* (2006.01)
  *A01K 1/015* (2006.01)
  *A61L 15/60* (2006.01)
  *B01J 20/30* (2006.01)
  *B01J 20/32* (2006.01)
  *G01N 21/78* (2006.01)
  *G01N 33/493* (2006.01)
  *B29B 9/08* (2006.01)

(52) U.S. Cl.
  CPC .......... *B01J 20/24* (2013.01); *B01J 20/261* (2013.01); *B01J 20/262* (2013.01); *B01J 20/28011* (2013.01); *B01J 20/28016* (2013.01); *B01J 20/28069* (2013.01); *B01J 20/3021* (2013.01); *B01J 20/3028* (2013.01); *B01J 20/321* (2013.01); *B01J 20/3212* (2013.01); *B01J 20/3225* (2013.01); *B01J 20/3293* (2013.01); *G01N 21/78* (2013.01); *G01N 33/493* (2013.01); *B01J 2220/445* (2013.01); *B01J 2220/49* (2013.01); *B01J 2220/68* (2013.01); *B29B 9/08* (2013.01)

(58) Field of Classification Search
  CPC ............ B01J 20/262; B01J 20/28011; B01J 20/28016; B01J 20/28069; B01J 20/3021; B01J 20/3028; B01J 20/321; B01J 20/3212; B01J 20/3225; B01J 20/3293; G01N 33/493; G01N 21/78
  See application file for complete search history.

(56) References Cited

U.S. PATENT DOCUMENTS

| | | |
|---|---|---|
| 4,883,021 A | 11/1989 | Ducharme |
| 5,064,615 A | 11/1991 | Mangold et al. |
| 5,468,450 A | 11/1995 | Michael |
| 5,735,232 A | 4/1998 | Lang |
| 5,760,121 A | 6/1998 | Beall |
| 6,039,004 A | 3/2000 | Goss |
| 6,042,839 A | 3/2000 | Lahanas |
| 6,197,849 B1 | 3/2001 | Michl |
| 6,228,903 B1 | 5/2001 | Beall |
| 6,261,640 B1 | 7/2001 | Pinnavaia |
| 6,271,297 B1 | 8/2001 | Ishida |
| 6,376,034 B1 | 4/2002 | Brander |
| 6,399,690 B2 | 6/2002 | Lan |
| 6,407,155 B1 | 6/2002 | Qian |
| 6,414,069 B1 | 7/2002 | Pinnavaia |
| 6,521,690 B1 | 2/2003 | Ross |
| 6,579,927 B1 | 6/2003 | Fischer |
| 6,586,500 B2 | 7/2003 | Bagrodia |
| 6,730,719 B2 | 5/2004 | Powell |
| 7,429,009 B2 | 9/2008 | Nagasawa |
| 7,533,630 B2 | 5/2009 | Steckel |
| 9,547,000 B2 | 1/2017 | Gravel-Lacroix |
| 2002/0165305 A1 | 11/2002 | Knudson, Jr. |
| 2002/0169246 A1 | 11/2002 | Barbee |
| 2003/0060555 A1 | 3/2003 | Lorah |
| 2003/0108497 A1 | 6/2003 | Chevalier |
| 2003/0134942 A1 | 7/2003 | Lee |
| 2003/0170905 A1 | 9/2003 | Kamyshny |
| 2008/0022940 A1 | 1/2008 | Kirsch |
| 2009/0217882 A1 | 9/2009 | Jenkins |

FOREIGN PATENT DOCUMENTS

| | | |
|---|---|---|
| CA | 2462053 | 9/2004 |
| CA | 2607753 | 5/2008 |
| CA | 2607758 | 5/2008 |
| CA | 2737489 | 11/2010 |
| EP | 1327435 | 7/2003 |
| GB | 1240884 | 7/1971 |
| JP | 2003160694 | 6/2003 |
| JP | 2010041966 | 2/2010 |
| WO | WO 199858533 | 12/1998 |
| WO | WO 2004043663 | 5/2004 |
| WO | 2010133001 A1 | 11/2010 |
| WO | WO 2010133001 | 11/2010 |
| WO | 2014032175 A1 | 3/2014 |
| WO | 2015127528 A1 | 9/2015 |

30 mins after contact 2h after contact 18h after contact 30 mins after contact 2h after contact 18h after contact 6h30 after contact 22h after contact

WATER-ABSORBING MATERIAL AND USES THEREOF

CROSS-REFERENCE TO RELATED APPLICATIONS

This application is a National Stage application of International Application No. PCT/CA2016/051037, filed Sep. 1, 2016, which claims the benefit of U.S. Provisional Application No. 62/316,639, filed Apr. 1, 2016.

FIELD

The technical field relates to absorbent materials, and more specifically relates to a water-absorbing material that can be used for purposes such as chromogenic detection of chemical and/or biological species.

BACKGROUND

Water-absorbent materials such as absorbent materials including polysaccharides can be employed in different fields. For example, water-absorbent materials can be used in pet litter, household articles, sealing materials, humectants for agricultural products for soil conditioning, oil-drilling, anti-condensation coatings, water-storing materials in agriculture/horticulture, absorbent paper products, bandages and surgical pads, disposable sanitary products (such as diapers, incontinence articles, feminine hygiene products, airlaids and absorbent dressings), wound dressings, or as chemical absorbents.

Among known water absorbent materials, polysaccharides and polysaccharide mixtures have been widely used, alone or in conjunction with inorganic absorbent materials such as phyllosilicates. The more widely used polysaccharides are typically based on starch and/or cellulose, and the phyllosilicates can for example include bentonite.

Many processes for manufacturing such absorbent materials are known, and include for example granulation. A widely-used granulation process is wet granulation, including for example high shear mixture granulation, fluid bed granulation, extrusion-spheronization and spray drying. Wet granulation is known to have many advantages, such as increasing the density of the material, providing a better distribution of a compound of interest within the material compared to some other methods, reducing dust hazards, preventing segregation of powders and increasing the hydrophilicity of otherwise hydrophobic materials.

However, wet granulation also has many disadvantages. For example, granulation can be costly, as it often requires qualified personnel, large operation space and special equipment. Wet granulation also typically has a high energy requirement. Loss of material can occur during various stages of processing, and incompatibilities between the formulation components are typically aggravated during processing. More specifically, high shear mixture granulation can sometimes lead to mechanical degradation of the material.

Fluid bed granulation and extrusion-spheronization are often labor-intensive and time consuming, and have various other challenges.

There is therefore still a need for a process and apparatus for manufacturing water-absorbing materials that overcome at least one of the above-mentioned issues.

Water-absorbent materials can also be used as a support for diagnostic agents for humans or animals. For example, it is known to use diagnostic agents, incorporated into test strips, beads or particles, for detection purposes. Usually, such test strips consist of an absorbent carrier made from fibrous or non-woven material, in the simplest case filter paper, which is coated or impregnated with the detection reagents. The detection reagents may include a chromogenic compound as an indicator, and a trigger compound to transform the chromogenic indicator into a chromogenically active compound in the presence of the compound to be detected.

For example, feline urinary tract disease can be a serious condition for cats. In feline urinary tract disease, crystals of magnesium ammonium phosphate can precipitate in the cat's urinary tract and cause obstruction. If untreated, the obstruction can lead to intense pain and can often be fatal within days. In some cases, upon observing feline urinary tract disease symptoms—such as bloody urine and urination discomfort and straining—cat owners often consult their veterinarian who may be able to provide treatments, which may be expensive. However, many cats with feline urinary tract disease do not show any obvious symptoms, which is why this disease has been referred to as a "silent killer".

Another example of a serious condition for cats is diabetes. Diabetes strikes about 1 in 400 cats and has become increasingly common. Symptoms of diabetes in cats are similar to those in humans, and about 80% to 95% of diabetic cats experience something similar to type-2 diabetes in humans. Cats suffering of diabetes usually become severely insulin-dependent by the time symptoms are diagnosed. In cats suffering from type-2 diabetes, early treatment can sometimes lead to diabetic remission, in which the cat no longer needs injected insulin. If left untreated, the condition leads to increasingly weak cats, malnutrition, ketoacidosis and/or dehydration, and eventually death.

Early detection of diseases or conditions in animals or humans is therefore of paramount importance in facilitating treatment, lessening the likelihood of severe complications or aggravations, and reducing the cost of treatment.

Providing a reliable occult blood or glucose detection system in animal litter itself also has many problems and challenges. For example, the test indicator material should be stable when exposed to a wide variety of ambient conditions, be they dry or humid, and over a wide range of temperatures. Such stability is quite often difficult to achieve.

A further problem with many known test indicators is that pet owners are insufficiently observant or sophisticated to appreciate the positive indication, such as a color change, before the indicator decays. Many known indicators do not stay at the changed color for a sufficient period of time to allow pet owners to reliably recognize the indicated health issue.

An additional problem with various detection reagents mixed with animal litter is that the test reagents give off sufficient scent such that cats, which have an extraordinary sense of smell, recognize the odor change in their litter and thus tend to shy away from the litter. As will be appreciated, this not only defeats the purpose of a convenient detector but can also cause unwanted excretory mishaps. Thus, test reagents with significant, offensive or upsetting odors—both to the user and the cat—have many disadvantages.

A further problem with known detection reagents is poor shelf life stability, particularly if combined with an animal litter for storage as a single mixture. Poor stability leads to disadvantages in the ability to store, transport, display, purchase and use the detection-litter combination.

Similar problems also exist for the detection chemical compounds indicative of various conditions such as glycosuria, ketonuria, liver conditions, bacterial infections etc., in humans or animals, and many challenges still exist.

SUMMARY

Various water-absorbing materials, processes for production thereof, and uses thereof will be described below. The water-absorbing material can include an absorptive matrix and a detection composition provided within the matrix for detecting a substance that may be indicative of a disease or condition. The water-absorbing material can also include other substances for pre-determined purposes.

In some implementations, there is provided a process for manufacturing a water-absorbing material, including: providing an absorptive powder including a water-absorbing polysaccharide onto a surface, thereby obtaining a powder bed; releasing an aqueous solution from a solution dispenser so as to contact the powder bed, thereby forming a solution-impregnated humid material; maintaining the solution-impregnated humid material supported by the surface and in substantially shear-less conditions until the solution-impregnated humid material agglomerates to produce an agglomerated humid material; and drying the agglomerated humid material, thereby forming the water-absorbing material.

In some implementations, the surface is a substantially planar surface.

In some implementations, the process further includes displacing the solution-impregnated humid material away from the solution dispenser.

In some implementations, the powder bed is in translation relative to the solution dispenser.

In some implementations, releasing the aqueous solution includes pouring the aqueous solution under gravity onto the powder bed.

In some implementations, releasing the aqueous solution is performed from a distance of at most 10 cm above the powder bed.

In some implementations, releasing the aqueous solution is performed such that the aqueous solution has a velocity of at most 1.5 m/s upon contacting the powder bed.

In some implementations, the step of releasing the aqueous solution is performed such that a first portion of the absorptive powder is used to form the agglomerated humid material and a second portion of the absorptive powder remains as residual powder.

In some implementations, the process further includes separating the residual powder from the agglomerated humid material.

In some implementations, separating the residual powder from the agglomerated humid material includes sieving.

In some implementations, the process further includes recycling at least a portion of the residual powder for re-use as part of the powder bed.

In some implementations, the surface extends substantially horizontally.

In some implementations, the process further includes controlling a thickness of the powder bed.

In some implementations, the thickness is of about 1 cm to about 5 cm.

In some implementations, the absorptive powder further includes a second polysaccharide mixed with the water-absorbing polysaccharide.

In some implementations, the second polysaccharide includes a crystalline polysaccharide.

In some implementations, the crystalline polysaccharide includes cellulose, a cellulose derivative or a mixture thereof.

In some implementations, the cellulose includes microcrystalline cellulose (MCC), nanocrystalline cellulose (NCC) or a mixture thereof.

In some implementations, the water-absorbing polysaccharide includes a starch, a modified starch, a cellulose derivative, an alginate, an alginate derivative, a gelling polysaccharide or a mixture thereof.

In some implementations, the water-absorbing polysaccharide includes pregelatinized starch.

In some implementations, the particles of water-absorbing material have an effective porosity of about 0.5 mL/g to about 2.0 mL/g.

In some implementations, the effective porosity is of about 0.8 mL/g to about 1.2 mL/g.

In some implementations, the effective porosity is of about 0.9 mL/g to about 1.1 mL/g.

In some implementations, the particles of water-absorbing material are provided with pores having an equivalent diameter greater than about 20 µm.

In some implementations, the equivalent diameter is of about 20 µm to about 40 µm.

In some implementations, the equivalent diameter is of about 20 µm to about 30 µm.

In some implementations, the particles of water-absorbing material have a free swelling capacity greater than about 900%.

In some implementations, the particles of water-absorbing material have a free swelling capacity greater than about 1000%.

In some implementations, the drying includes drying under vacuum.

In some implementations, the drying includes drying by heating.

In some implementations, the drying is performed by heating to temperatures ranging from ambient temperature to about 65° C.

In some implementations, the particles of water-absorbing material have a density of about 0.20 g/cm$^3$ to about 0.39 g/cm$^3$.

In some implementations, the density is of about 0.25 g/cm$^3$ to about 0.35 g/cm$^3$.

In some implementations, the density is of about 0.30 g/cm$^3$ to about 0.35 g/cm$^3$.

In some implementations, the absorptive powder further includes at least one of magnesium stearate, celite, magnesium carbonate and talc.

In some implementations, the aqueous solution is released in the form of discrete drops onto the powder bed such that: the solution-impregnated humid material is produced in the form of solution-impregnated humid particles; the agglomerated humid material is produced in the form of agglomerated humid particles; and the water-absorbing material is produced in the form of particles of water-absorbing material.

In some implementations: the water-absorbing material is a chromogenic absorbent material for detecting a detectable substance in an animal excretion; and the aqueous solution is a chromogenic solution including: a trigger agent; and a chromogenic indicator oxidizable into a colored and/or fluorescent substance in the presence of the trigger agent and the detectable substance.

In some implementations, the detectable substance includes a peroxidase or a pseudoperoxidase; and the trigger agent includes an oxidizing agent responsive to peroxidatic/pseudoperoxidatic activity in the animal excretion.

In some implementations, the detectable substance includes blood.

In some implementations, the oxidizing agent includes a hydroperoxide, a hydroperoxide precursor or a mixture thereof.

In some implementations, the detectable substance includes glucose; and the trigger agent includes a catalytic system including an oxido-reductase and a peroxidase or a pseudoperoxidase.

In some implementations, the oxido-reductase includes glucose oxidase.

In some implementations, the peroxidase includes horseradish peroxidase.

In some implementations, there is provided a system for manufacturing particles of water-absorbing material, including: a surface; a powder feeder configured to release an absorptive powder mixture onto the surface, thereby forming a powder bed; a solution dispenser for dripping discrete drops of an aqueous solution onto the powder bed, such that the drops are impregnated with respective amounts of the absorptive powder mixture, thereby forming solution-impregnated humid particles isolated from each other and supported by the surface; and a drying unit for drying the solution-impregnated humid particles, thereby forming the particles of water-absorbing material.

In some implementations, the surface is a substantially planar surface.

In some implementations, the surface is a conveying surface.

In some implementations, the conveying surface is configured to displace the solution-impregnated humid material away from the solution dispenser.

In some implementations, the conveying surface is configured to displace the powder bed in a translation movement relative to the solution dispenser.

In some implementations, the solution dispenser is configured to release the aqueous solution from a distance of at most 10 cm above the powder bed.

In some implementations, the solution dispenser is configured to release the aqueous solution such that the aqueous solution has a velocity of at most 1.5 m/s upon contacting the powder bed.

In some implementations, the solution dispenser releases the aqueous solution such that a first portion of the absorptive powder is used to form the agglomerated humid material and a second portion of the absorptive powder remains on the surface as residual powder.

In some implementations, the system further includes a first sieve located on or embedded in the conveying surface, for recycling of the residual powder.

In some implementations, the system further includes a second sieve located on or embedded in the conveying surface, for recovering the solution-impregnated humid particles.

In some implementations, there is provided a process for manufacturing particles of water-absorbing material, including:
  providing an absorptive powder including a water-absorbing polysaccharide onto a surface, thereby obtaining a powder bed;
  dripping an aqueous solution as discrete drops from a solution dispenser so as to contact the powder bed and become impregnated by the absorptive powder to form corresponding solution-impregnated humid particles;
  handling the solution-impregnated humid particles to remain isolated from each other until the solution-impregnated humid particles agglomerate, thereby forming respective agglomerated humid particles; and
  drying the stable humid particles to produce the particles of water-absorbing material.

In some implementations, the powder bed and the aqueous solution are contacted such that the solution-impregnated humid material remains in spaced relation with respect to the surface.

In some implementations, the powder bed and the aqueous solution are contacted such that substantially all of the aqueous solution remains in the solution-impregnated humid particle.

In some implementations, there is provided a process for manufacturing particles of water-absorbing material, including:
  providing an absorptive powder including a water-absorbing polysaccharide onto a surface, thereby obtaining a powder bed;
  releasing an aqueous solution in the form of discrete drops from a solution dispenser so as to contact the powder bed, thereby forming solution-impregnated humid particles;
  maintaining the solution-impregnated humid particles supported by the surface and in substantially shear-less conditions until the solution-impregnated humid particles agglomerate to produce agglomerated humid particles; and
  drying the agglomerated humid particles, thereby forming the particles of water-absorbing material.

In some implementations, there is provided a process for manufacturing particles of chromogenic absorbent material for an animal litter, the process including:
  providing an absorptive powder including a water-absorbing polysaccharide onto a surface, thereby obtaining a powder bed;
  providing a chromogenic solution by addition of a chromogenic agent and an oxidizing agent or by addition of the chromogenic agent and a first catalytic compound, into a solvent;
  releasing the chromogenic solution in the form of discrete drops from a solution dispenser so as to contact the powder bed, thereby forming a solution-impregnated humid material;
  maintaining the solution-impregnated humid material supported by the surface and in substantially shear-less conditions until the solution-impregnated humid material agglomerates to produce agglomerated humid particles; and
  drying the agglomerated humid particles, thereby forming the particles of chromogenic absorbent material.

In some implementations, the aqueous solution comprises a colorimetric pH indicator and the water-absorbing material is a chromogenic absorbent material for measuring the pH of a substance contacting the water-absorbing material.

In some implementations, the pH indicator includes methyl violet, thymol blue, benzyl orange, bromophenol blue, congo red, methyl orange, methyl red, bromocresol purple, bromothymol blue, phenol red, cresol red, thymol blue, phenolphthalein, tymolphthalein, alizarin yellow R or combinations thereof.

In some implementations, the pH indicator includes a Bogen universal indicator.

In some implementations, there is provided a chromogenic absorbent material for an animal litter, comprising:
  a chromogenic indicator comprising a pH indicator for determining the pH of an animal excretion; and
  an absorptive material which is porous, for absorbing the animal excretion, the absorptive material comprising:

a water-absorbing polysaccharide providing absorptive properties to the chromogenic absorbent material; and a second polysaccharide providing structural integrity to the chromogenic absorbent material.

In some implementations, the second polysaccharide comprises a crystalline polysaccharide.

In some implementations, the crystalline polysaccharide comprises cellulose, a cellulose derivative or mixtures thereof.

In some implementations, the cellulose comprises microcrystalline cellulose (MCC), nanocrystalline cellulose (NCC), or a mixture thereof.

In some implementations, the absorptive material comprises:
about 35 wt. % to about 65 wt. % of the water-absorbing polysaccharide; and
about 35 wt. % to about 65 wt. % of the second polysaccharide.

In some implementations, the absorptive material comprises:
about 45 wt. % to about 55 wt. % of the water-absorbing polysaccharide; and
about 45 wt. % to about 55 wt. % of the second polysaccharide.

In some implementations, there is provided a chromogenic absorbent material for an animal litter, comprising:
a chromogenic indicator comprising a pH indicator for determining the pH of an animal excretion; and
an absorptive material which is porous, for absorbing the animal excretion, the absorptive material comprising a water-absorbing polysaccharide,
wherein the chromogenic absorbent material has a density of about 0.20 g/cm$^3$ to about 0.39 g/cm$^3$.

In some implementations, the density of the chromogenic absorbent material is about 0.25 g/cm$^3$ to about 0.35 g/cm$^3$.

In some implementations, the density of the chromogenic absorbent material is about 0.30 g/cm$^3$ to about 0.35 g/cm$^3$.

In some implementations, there is provided a chromogenic absorbent material for an animal litter, comprising:
a chromogenic indicator comprising a pH indicator for determining the pH of an animal excretion; and
an absorptive material which is porous, for absorbing the animal excretion, the absorptive material comprising a water-absorbing polysaccharide,
wherein the chromogenic absorbent material is a porous material having an effective porosity of about 0.5 mL/g to about 2.0 mL/g.

In some implementations, the effective porosity is of about 0.6 mL/g to about 1.5 mL/g.

In some implementations, the effective porosity is of about 0.8 mL/g to about 1.2 mL/g.

In some implementations, the effective porosity is of about 0.9 mL/g to about 1.1 mL/g.

In some implementations, the chromogenic absorbent material is provided with pores having an equivalent diameter greater than about 20 μm.

In some implementations, the chromogenic absorbent material is provided with pores having an equivalent diameter of about 20 μm to about 40 μm.

In some implementations, the chromogenic absorbent material is provided with pores having an equivalent diameter of about 20 μm to about 30 μm.

In some implementations, the material has a free swelling capacity greater than about 900%.

In some implementations, the material has a free swelling capacity greater than about 1000%.

In some implementations, there is provided a chromogenic absorbent material for an animal litter, comprising:
a chromogenic indicator comprising a pH indicator for determining the pH of an animal excretion; and
an absorptive material which is porous, for absorbing the animal excretion, the absorptive material comprising:
a water-absorbing polysaccharide providing absorptive properties to the chromogenic absorbent material; and
a superabsorbent polymer (SAP).

In some implementations, the absorptive material comprises up to about 3 wt. % of the SAP.

In some implementations, the absorptive material comprises about 1 wt. % to about 3 wt. % of the SAP.

In some implementations, the absorptive material comprises about 1 wt. % to about 2 wt. % of the SAP.

In some implementations, the SAP comprises at least one of a poly(acrylic acid) and a poly(methacrylic acid), or a salt thereof.

In some implementations, there is provided a chromogenic absorbent material for an animal litter, comprising:
a chromogenic indicator comprising a pH indicator for determining the pH of an animal excretion; and
an absorptive material which is porous, for absorbing the animal excretion, the absorptive material comprising:
a water-absorbing polysaccharide providing absorptive properties to the chromogenic absorbent material; and
a second polysaccharide providing structural integrity to the chromogenic absorbent material,
wherein the chromogenic absorbent material is a porous material having:
an effective porosity of about 20% to about 40%; and
a density of about 0.20 g/cm$^3$ to about 0.39 g/cm$^3$.

In some implementations, the water-absorbing polysaccharide comprises a starch, a modified starch, a cellulose derivative or a gelling polysaccharide, or a mixture thereof.

In some implementations, the water-absorbing polysaccharide comprises pregelatinized starch.

In some implementations, the cellulose derivative comprises a cellulose ester or a cellulose ether, or a mixture thereof.

In some implementations, the cellulose derivative comprises carboxymethyl cellulose (CMC).

In some implementations, the gelling polysaccharide comprises agar-agar, guar or xanthan, or a mixture thereof.

In some implementations, the chromogenic indicator is distributed within the absorptive material.

In some implementations, the pH indicator includes methyl violet, thymol blue, benzyl orange, bromophenol blue, congo red, methyl orange, methyl red, bromocresol purple, bromothymol blue, phenol red, cresol red, thymol blue, phenolphthalein, tymolphthalein, alizarin yellow R or combinations thereof.

In some implementations, the pH indicator includes a Bogen universal indicator.

In some implementations, there is provided the use of the chromogenic absorbent material as chromogenic particles in combination with animal litter.

In some implementations, the animal litter comprises clay based particles, cellulosic particles, perlite based particles, silica based particles, corn based particles, paper based particles or wheat based particles or a combination thereof.

In some implementations, the clay based particles comprise montmorillonite.

In some implementations, the clay based particles comprise bentonite.

In some implementations, there is provided the use of the chromogenic absorbent material as described herein for measuring the pH in animal excretions.

In some implementations, the chromogenic particles are substantially evenly distributed on a top surface of the animal litter.

In some implementations, the chromogenic particles are substantially evenly distributed within the animal litter.

In some implementations, the chromogenic particles comprise pellets, granules, disks, squares according to their process of manufacture.

In some implementations, a chromogenic absorbent material for detecting a detectable substance in a water-containing medium is provided. The chromogenic absorbent material includes: a trigger agent; a chromogenic indicator convertible into a chromogenically active substance in the presence of the trigger agent and the detectable substance; and an absorptive material which is porous, for absorbing the water-containing medium, the absorptive material comprising: a water-absorbing polysaccharide providing absorptive properties to the chromogenic absorbent material; and a second polysaccharide providing structural integrity to the chromogenic absorbent material, the trigger agent, the chromogenic indicator and the detectable substance being unreactive to the absorptive material.

In some implementations, the second polysaccharide comprises a crystalline polysaccharide.

In some implementations, the crystalline polysaccharide comprises cellulose, a cellulose derivative or mixtures thereof.

In some implementations, the cellulose comprises microcrystalline cellulose (MCC), nanocrystalline cellulose (NCC), or a mixture thereof.

In some implementations, the absorptive material comprises:
  about 35 wt. % to about 65 wt. % of the water-absorbing polysaccharide; and
  about 35 wt. % to about 65 wt. % of the second polysaccharide.

In some implementations, the absorptive material comprises:
  about 45 wt. % to about 55 wt. % of the water-absorbing polysaccharide; and
  about 45 wt. % to about 55 wt. % of the second polysaccharide.

In some implementations, the material has a density of about 0.20 g/cm$^3$ to about 0.39 g/cm$^3$.

In some implementations, the density is about 0.25 g/cm$^3$ to about 0.35 g/cm$^3$.

In some implementations, the density is about 0.30 g/cm$^3$ to about 0.35 g/cm$^3$.

In some implementations, the material is a porous material having an effective porosity of about 0.5 mL/g to about 2.0 mL/g.

In some implementations, the effective porosity is of about 0.6 mL/g to about 1.5 mL/g.

In some implementations, the effective porosity is of about 0.8 mL/g to about 1.2 mL/g.

In some implementations, the effective porosity is of about 0.9 mL/g to about 1.1 mL/g.

In some implementations, the chromogenic absorbent material is provided with pores having an equivalent diameter greater than about 20 μm.

In some implementations, the equivalent diameter is of about 20 μm to about 40 μm.

In some implementations, the equivalent diameter is of about 20 μm to about 30 μm.

In some implementations, the material has a free swelling capacity greater than about 900%.

In some implementations, the material has a free swelling capacity greater than about 1000%.

In some implementations, the absorptive material further comprises a superabsorbent polymer (SAP).

In some implementations, the absorptive material comprises up to about 3 wt. % of the SAP.

In some implementations, the absorptive material comprises about 1 wt. % to about 3 wt. % of the SAP.

In some implementations, the absorptive material comprises about 1 wt. % to about 2 wt. % of the SAP.

In some implementations, the SAP comprises at least one of a poly(acrylic acid) and a poly(methacrylic acid), or a salt thereof.

In some implementations, the chromogenic absorbent material has a pore density greater than about 20%.

In some implementations, there is provided a chromogenic absorbent material for detecting a detectable substance in a water-containing medium. The chromogenic absorbent material includes: a trigger agent; a chromogenic indicator convertible into a chromogenically active substance in the presence of the trigger agent and the detectable substance; and an absorptive material which is porous, for absorbing the water-containing medium, the absorptive material comprising a water-absorbing polysaccharide providing absorptive properties to the chromogenic absorbent material, wherein the chromogenic absorbent material has a density of about 0.20 g/cm$^3$ to about 0.39 g/cm$^3$, the trigger agent, the chromogenic indicator and the detectable substance being unreactive to the absorptive material.

In some implementations, the density is about 0.25 g/cm$^3$ to about 0.35 g/cm$^3$.

In some implementations, the density is about 0.30 g/cm$^3$ to about 0.35 g/cm$^3$.

In some implementations, the material is a porous material having an effective porosity of about 0.5 mL/g to about 2.0 mL/g.

In some implementations, the effective porosity is of about 0.6 mL/g to about 1.5 mL/g.

In some implementations, the effective porosity is of about 0.8 mL/g to about 1.2 mL/g.

In some implementations, the effective porosity is of about 0.9 mL/g to about 1.1 mL/g.

In some implementations, the chromogenic absorbent material is provided with pores having an equivalent diameter greater than about 20 μm.

In some implementations, the equivalent diameter is of about 20 μm to about 40 μm.

In some implementations, the equivalent diameter is of about 20 μm to about 30 μm.

In some implementations, the material has a free swelling capacity greater than about 900%.

In some implementations, the material has a free swelling capacity greater than about 1000%.

In some implementations, the absorptive material further comprises a superabsorbent polymer (SAP).

In some implementations, the absorptive material comprises up to about 3 wt. % of the SAP.

In some implementations, the absorptive material comprises about 1 wt. % to about 3 wt. % of the SAP.

In some implementations, the absorptive material comprises about 1 wt. % to about 2 wt. % of the SAP.

In some implementations, the SAP comprises at least one of a poly(acrylic acid) and a poly(methacrylic acid), or a salt thereof.

In some implementations, the chromogenic absorbent material has a pore density greater than about 20%.

In some implementations, the absorptive material further comprises a second polysaccharide providing structural integrity to the chromogenic absorbent material.

In some implementations, n the second polysaccharide comprises a crystalline polysaccharide.

In some implementations, the crystalline polysaccharide comprises cellulose, a cellulose derivative or mixtures thereof.

In some implementations, the cellulose comprises microcrystalline cellulose (MCC), nanocrystalline cellulose (NCC), or a mixture thereof.

In some implementations, the absorptive material comprises:
about 35 wt. % to about 65 wt. % of the water-absorbing polysaccharide; and
about 35 wt. % to about 65 wt. % of the second polysaccharide.

In some implementations, the absorptive material comprises:
about 45 wt. % to about 55 wt. % of the water-absorbing polysaccharide; and
about 45 wt. % to about 55 wt. % of the second polysaccharide.

In some implementations, there is provided a chromogenic absorbent material for detecting a detectable substance in a water-containing medium The chromogenic absorbent material includes: a trigger agent; a chromogenic indicator convertible into a chromogenically active substance in the presence of the trigger agent and the detectable substance; and an absorptive material which is porous, for absorbing the water-containing medium, the absorptive material comprising a water-absorbing polysaccharide providing absorptive properties to the chromogenic absorbent material, wherein the chromogenic absorbent material is a porous material having an effective porosity of about 0.5 mL/g to about 2.0 mL/g, the trigger agent, the chromogenic indicator and the detectable substance being unreactive to the absorptive material.

In some implementations, the material has a density of about 0.20 g/cm$^3$ to about 0.39 g/cm$^3$.

In some implementations, the density is about 0.25 g/cm$^3$ to about 0.35 g/cm$^3$.

In some implementations, the density is about 0.30 g/cm$^3$ to about 0.35 g/cm$^3$.

In some implementations, the effective porosity is of about 0.6 mL/g to about 1.5 mL/g.

In some implementations, the effective porosity is of about 0.8 mL/g to about 1.2 mL/g.

In some implementations, the effective porosity is of about 0.9 mL/g to about 1.1 mL/g.

In some implementations, the chromogenic absorbent material is provided with pores having an equivalent diameter greater than about 20 μm.

In some implementations, the equivalent diameter is of about 20 μm to about 40 μm.

In some implementations, the equivalent diameter is of about 20 μm to about 30 μm.

In some implementations, the material has a free swelling capacity greater than about 900%.

In some implementations, the material has a free swelling capacity greater than about 1000%.

In some implementations, the absorptive material further comprises a superabsorbent polymer (SAP).

In some implementations, the absorptive material comprises up to about 3 wt. % of the SAP.

In some implementations, the absorptive material comprises about 1 wt. % to about 3 wt. % of the SAP.

In some implementations, the absorptive material comprises about 1 wt. % to about 2 wt. % of the SAP.

In some implementations, the SAP comprises at least one of a poly(acrylic acid) and a poly(methacrylic acid), or a salt thereof.

In some implementations, the chromogenic absorbent material has a pore density greater than about 20%.

In some implementations, the absorptive material further comprises a second polysaccharide providing structural integrity to the chromogenic absorbent material.

In some implementations, the second polysaccharide comprises a crystalline polysaccharide.

In some implementations, the crystalline polysaccharide comprises cellulose, a cellulose derivative or mixtures thereof.

In some implementations, the cellulose comprises microcrystalline cellulose (MCC), nanocrystalline cellulose (NCC), or a mixture thereof.

In some implementations, the absorptive material comprises:
about 35 wt. % to about 65 wt. % of the water-absorbing polysaccharide; and
about 35 wt. % to about 65 wt. % of the second polysaccharide.

In some implementations, the absorptive material comprises:
about 45 wt. % to about 55 wt. % of the water-absorbing polysaccharide; and
about 45 wt. % to about 55 wt. % of the second polysaccharide.

In some implementations: the detectable substance is haemoglobin; the trigger agent is an oxidizing agent responsive to peroxidatic/pseudoperoxidatic activity in the water-containing medium; and the chromogenic indicator is responsive to the oxidizing activity of the oxidizing agent.

In some implementations, the water-absorbing polysaccharide comprises a starch, a modified starch, a cellulose derivative or a gelling polysaccharide, or a mixture thereof.

In some implementations, the water-absorbing polysaccharide comprises pregelatinized starch.

In some implementations, the cellulose derivative comprises a cellulose ester or a cellulose ether, or a mixture thereof.

In some implementations, the cellulose derivative comprises carboxymethyl cellulose (CMC).

In some implementations, the gelling polysaccharide comprises agar-agar, guar or xanthan, or a mixture thereof.

7 In some implementations, the oxidizing agent comprises a hydroperoxide or a hydroperoxide precursor, or a combination thereof.

In some implementations, the hydroperoxide comprises hydrogen peroxide, cumene hydroperoxide or diisopropylbenzene dihydroperoxide, or a combination thereof.

In some implementations, the oxidizing agent and the chromogenic indicator are distributed within the absorptive material.

In some implementations, the chromogenic indicator comprises a benzidine-type compound.

In some implementations, the benzidine-type compound comprises 3,3',5,5'-tetramethylbenzidine.

In some implementations, the material further comprises a buffering agent, a stabilizer, a metal scavenger agent or a color enhancer or a combination thereof.

In some implementations, the color enhancer comprises 6-methoxyquinoline, lepidin, phenol derivatives, nitrobenzene, N-methylpyrrolidone or ethylene carbonate or a combination thereof.

In some implementations, the buffering agent comprises citrate, sodium citrate, phosphate or acetate or a combination thereof.

In some implementations, the stabilizer comprises ammonium molybdate, polyethylene glycol, polyvinylpyrrolidone, polyethylene oxide or derivatives thereof or a combination thereof.

In some implementations, the metal-scavenger agent comprises ethylenediaminetetraacetic acid (EDTA) or EDTA sodium salt or a combination thereof.

In some implementations, the chromogenic indicator is responsive to the oxidizing agent by turning blue in presence of the peroxidatic/pseudoperoxidatic activity in the animal excretions.

In some implementations, the chromogenic absorbent material turns to blue in presence of the peroxidatic/pseudoperoxidatic activity after a contact time with the water-containing medium between about 10 seconds and about 30 min.

In some implementations, the chromogenic absorbent material turns to blue in presence of the peroxidatic/pseudoperoxidatic activity after a contact time with the animal excretion between about 10 seconds and about 1 min.

In some implementations, the detectable substance is glucose; the trigger agent is a catalytic system comprising: a first catalytic compound for in situ generation of an oxidizing agent responsive to peroxidatic/pseudoperoxidatic activity in an animal excretion, the oxidizing agent providing oxidizing activity; and a second catalytic compound for catalyzing the oxidation of the chromogenic indicator upon in situ generation of the oxidizing agent; and the chromogenic indicator is responsive to the oxidizing activity of the oxidizing agent.

In some implementations, the water-absorbing polysaccharide comprises a cellulose derivative, a gelling polysaccharide, or a mixture thereof.

In some implementations, the cellulose derivative is a cellulose ester or a cellulose ether, or a mixture thereof.

In some implementations, the cellulose derivative comprises carboxymethyl cellulose (CMC).

In some implementations, the gelling polysaccharide comprises agar-agar, guar or xanthan, or a mixture thereof.

In some implementations, the first catalytic compound comprises an oxido-reductase enzyme.

In some implementations, the oxido-reductase comprises glucose oxidase (GOx).

In some implementations, the oxidizing agent generated in situ is hydrogen peroxide.

In some implementations, the second catalytic compound comprises a peroxidase, a pseudoperoxidase, or a mixture thereof.

In some implementations, the peroxidase comprises horseradish peroxidase (HRP).

In some implementations, the first catalytic compound, the second catalytic compound and the chromogenic indicator are distributed within the absorptive material.

In some implementations, the chromogenic indicator comprises a benzidine-type compound.

In some implementations, the benzidine-type compound comprises 3,3',5,5'-tetramethylbenzidine.

In some implementations, the material further comprises a buffering agent, a stabilizer, a metal scavenger agent or a color enhancer or a combination thereof.

In some implementations, the color enhancer comprises 6-methoxyquinoline, lepidin, phenol derivatives, nitrobenzene, N-methylpyrrolidone or ethylene carbonate or a combination thereof.

In some implementations, the buffering agent comprises citrate, sodium citrate, phosphate or acetate or a combination thereof.

In some implementations, the stabilizer comprises ammonium molybdate, polyethylene glycol, polyvinylpyrrolidone, polyethylene oxide or derivatives thereof or a combination thereof.

In some implementations, the metal-scavenger agent comprises ethylenediaminetetraacetic acid (EDTA) or EDTA sodium salt or a combination thereof.

In some implementations, the chromogenic indicator is responsive to the oxidizing agent by turning blue in presence of the peroxidatic/pseudoperoxidatic activity in the animal excretions.

In some implementations, the chromogenic absorbent material turns to blue in presence of the peroxidatic/pseudoperoxidatic activity after a contact time with the water-containing medium between about 10 seconds and about 30 min.

In some implementations, the chromogenic absorbent material turns to blue in presence of the peroxidatic/pseudoperoxidatic activity after a contact time with the animal excretion between about 10 seconds and about 1 min.

In some implementations, the detectable substance is proteins; the trigger agent is an acidic buffer for protonating amino groups of the proteins; and the chromogenic indicator is a pH indicator responsive to the protonated amino groups of the proteins.

In some implementations, the water-absorbing polysaccharide comprises a starch, a modified starch, a cellulose derivative or a gelling polysaccharide, or a mixture thereof.

In some implementations, the water-absorbing polysaccharide comprises pregelatinized starch.

In some implementations, the cellulose derivative comprises a cellulose ester or a cellulose ether, or a mixture thereof.

In some implementations, the cellulose derivative comprises carboxymethyl cellulose (CMC).

In some implementations, the gelling polysaccharide comprises agar-agar, guar or xanthan, or a mixture thereof.

In some implementations, the proteins comprise albumin.

In some implementations, the acidic buffer comprises formic acid, acetic acid or a mixture thereof.

In some implementations, the pH indicator is tetrabromophenol blue, 3',3'',5',5''-tetrachlorophenol and/or 3,4,5,6-tetrabromosulfon-phthalein.

In some implementations, the acidic buffer and the chromogenic indicator are distributed within the absorptive material.

In some implementations, the detectable substance is ketone bodies; the trigger agent is an alkali buffer enabling the reaction between the ketone bodies and the chromogenic indicator; and the chromogenic indicator is a metal complex reactive to the ketone bodies and convertible into a chromogenically active substance by reaction with the ketone bodies.

In some implementations, the water-absorbing polysaccharide comprises a starch, a modified starch, a cellulose derivative or a gelling polysaccharide, or a mixture thereof.

In some implementations, the water-absorbing polysaccharide comprises pregelatinized starch.

In some implementations, the cellulose derivative comprises a cellulose ester or a cellulose ether, or a mixture thereof.

In some implementations, the cellulose derivative comprises carboxymethyl cellulose (CMC).

In some implementations, the gelling polysaccharide comprises agar-agar, guar or xanthan, or a mixture thereof.

In some implementations, the ketone bodies comprise at least one of acetoacetate, beta-hydroxybutyric acid and acetone.

In some implementations, the alkali buffer comprises NaOH, KOH or a mixture thereof.

In some implementations, the metal complex comprises sodium nitroprusside.

In some implementations, the alkali buffer and the chromogenic indicator are distributed within the absorptive material.

In some implementations, the detectable substance is bilirubin or a bilirubin derivative; the trigger agent is an acidic buffer for enabling the reaction between bilirubin glucuronide and the chromogenic indicator; and the chromogenic indicator is a precursor reactive to bilirubin glucuronide and convertible into a chromogenically active substance by reaction with the bilirubin glucuronide.

In some implementations, the water-absorbing polysaccharide comprises a starch, a modified starch, a cellulose derivative or a gelling polysaccharide, or a mixture thereof.

In some implementations, the water-absorbing polysaccharide comprises pregelatinized starch.

In some implementations, the cellulose derivative comprises a cellulose ester or a cellulose ether, or a mixture thereof.

In some implementations, the cellulose derivative comprises carboxymethyl cellulose (CMC).

In some implementations, the gelling polysaccharide comprises agar-agar, guar or xanthan, or a mixture thereof.

In some implementations, the bilirubin or birilubin derivative comprises birilubin glucuronide.

In some implementations, the acidic buffer comprises formic acid, acetic acid or a mixture thereof.

In some implementations, the precursor is a diazonium salt.

In some implementations, the diazonium salt is dichlorobenzene-diazonium tetrafluoroborate.

In some implementations, the acidic buffer and the chromogenic indicator are distributed within the absorptive material.

In some implementations, the detectable substance is nitrite ions (NO$_2^-$); the trigger agent is an acidic buffer for enabling the reaction between the nitrite ions and the chromogenic indicator; and the chromogenic indicator is a chromogenic system including: a first precursor reactive to the nitrite ions to form a second precursor; and a chromogenic activator compound reactive to the second precursor for forming a chromogenically active substance by reaction with the second precursor.

In some implementations, the water-absorbing polysaccharide comprises a starch, a modified starch, a cellulose derivative or a gelling polysaccharide, or a mixture thereof.

In some implementations, the water-absorbing polysaccharide comprises pregelatinized starch.

146. The material of claim 144 or 145, wherein the cellulose derivative comprises a cellulose ester or a cellulose ether, or a mixture thereof.

In some implementations, the cellulose derivative comprises carboxymethyl cellulose (CMC).

In some implementations, the gelling polysaccharide comprises agar-agar, guar or xanthan, or a mixture thereof.

In some implementations, the bilirubin or birilubin derivative comprises birilubin glucuronide.

In some implementations, the acidic buffer comprises formic acid, acetic acid or a mixture thereof.

In some implementations, the first precursor comprises an aromatic amine forming a diazonium salt upon reacting with the nitrite ions; and the second precursor comprises a quinoline for forming the chromogenically active substance upon reacting with the diazonium salt.

In some implementations, the diazonium salt comprises dichlorobenzene-diazonium tetrafluoroborate.

In some implementations, the quinoline comprises tetrahydrobenzoquinoline.

In some implementations, the detectable substance is leukocyte esterase; the trigger agent catalytically reacts in presence of the leucocyte esterase in order to form a precursor; and the chromogenic indicator is a diazonium compound reactive to the precursor in order to form a chromogenically active substance.

In some implementations, the water-absorbing polysaccharide comprises a starch, a modified starch, a cellulose derivative or a gelling polysaccharide, or a mixture thereof.

In some implementations, the water-absorbing polysaccharide comprises pregelatinized starch.

In some implementations, the cellulose derivative comprises a cellulose ester or a cellulose ether, or a mixture thereof.

In some implementations, the cellulose derivative comprises carboxymethyl cellulose (CMC).

In some implementations, the gelling polysaccharide comprises agar-agar, guar or xanthan, or a mixture thereof.

In some implementations, the trigger agent comprises indolecarboxylic acid ester, and the precursor is indoxyl.

In some implementations, the diazonium compound is a diazonium salt.

In some implementations, the diazonium salt comprises 2,6-dichlorobenzene-diazonium-tetrafluoroborate.

In some implementations, the detectable substance is cations present in urine; the trigger agent comprises an anionic polyelectrolyte and an alkaline buffer releasing protons in proportion to the cations present in solution; and the chromogenic indicator is bromothymol blue which turns yellow in the presence of a certain concentration of released protons.

In some implementations, the water-absorbing polysaccharide comprises a starch, a modified starch, a cellulose derivative or a gelling polysaccharide, or a mixture thereof.

In some implementations, the water-absorbing polysaccharide comprises pregelatinized starch.

In some implementations, the cellulose derivative comprises a cellulose ester or a cellulose ether, or a mixture thereof.

In some implementations, the cellulose derivative comprises carboxymethyl cellulose (CMC).

In some implementations, the gelling polysaccharide comprises agar-agar, guar or xanthan, or a mixture thereof.

In some implementations, the polyelectrolyte comprises poly (methylvinyl)ether/maleic anhydride or ethylene Glycol-bis(aminoethyl ether) tetraacetate (EGTA).

In some implementations, the alkaline buffer comprises NaOH or KOH.

In some implementations, the trigger agent is present in an amount which enables the bromothymol blue to turn to yellow when the urine specific gravity is greater than 1.030.

In some implementations, the trigger agent is present in an amount which enables the bromothymol blue to turn to yellow when the urine specific gravity is greater than 1.050.

In some implementations, there is provided an absorbent material for detecting a detectable substance in a water-containing medium. The material comprises: a trigger agent for detecting the presence of the detectable substance when a chromogenic indicator is added to the absorbent material, the chromogenic indicator being convertible into a chromogenically active substance in the presence of the trigger agent and the detectable substance; and an absorptive material which is porous, for absorbing the water-containing medium, the absorptive material including: a water-absorbing polysaccharide providing absorptive properties to the absorbent material; and a second polysaccharide providing structural integrity to the absorbent material, the trigger agent and the detectable substance being unreactive to the absorptive material.

In some implementations, there is provided an absorbent material for detecting a detectable substance in a water-containing medium. The material comprises: a trigger agent for detecting the presence of the detectable substance when a chromogenic indicator is added to the absorbent material, the chromogenic indicator being convertible into a chromogenically active substance in the presence of the trigger agent and the detectable substance; and an absorptive material which is porous, for absorbing the water-containing medium, the absorptive material comprising a water-absorbing polysaccharide providing absorptive properties to the absorbent material, wherein the chromogenic absorbent material has a density of about 0.20 g/cm$^3$ to about 0.39 g/cm$^3$, the trigger agent and the detectable substance being unreactive to the absorptive material.

In some implementations, there is provided an absorbent material for detecting a detectable substance in a water-containing medium. The material comprises: a trigger agent for detecting the presence of the detectable substance when a chromogenic indicator is added to the absorbent material, the chromogenic indicator being convertible into a chromogenically active substance in the presence of the trigger agent and the detectable substance; and an absorptive material which is porous, for absorbing the water-containing medium, the absorptive material comprising a water-absorbing polysaccharide providing absorptive properties to the absorbent material, wherein the chromogenic absorbent material is a porous material having an effective porosity of about 0.5 mL/g to about 2.0 mL/g, the trigger agent and the detectable substance being unreactive to the absorptive material.

In some implementations, the material has any of the features described herein.

In some implementations, the material described herein may be used for the detection of blood.

In some implementations, the material described herein may be used for the detection of glucose.

In some implementations, the material described herein may be used for the detection of proteins.

In some implementations, the material described herein may be used for the detection of ketone bodies.

In some implementations, the material described herein may be used for the detection of bilirubin.

In some implementations, the material described herein may be used for the detection of nitrites.

In some implementations, the material described herein may be used for the detection of leukocytes.

In some implementations, the material described herein may be used for measuring specific gravity in urine.

In some implementations, the material described herein may be used for the detection of ovulation.

In some implementations, the material described herein may be used for the detection of bacteria.

In some implementations, the material described herein may be used for the detection of a virus.

In some implementations, the material described herein may be used for the detection of yeast.

In some implementations, the material described herein may be used for the detection of fungi.

In some implementations, the water-containing medium is an excretion.

In some implementations, the excretion comprises urine.

In some implementations, the excretion is an animal excretion.

In some implementations, the material is for use in an animal litter.

In some implementations, the animal litter comprises cat litter or a puppy pad.

In some implementations, the water-containing medium is an excretion.

In some implementations, the excretion comprises urine.

In some implementations, the excretion is an animal excretion.

In some implementations, the excretion is in an animal litter.

In some implementations, the animal litter comprises cat litter or a puppy pad.

In some implementations, there is provided a process for manufacturing a water-absorbing material, comprising:
  providing an absorptive powder comprising a water-absorbing polysaccharide onto a surface, thereby obtaining a powder bed;
  releasing an aqueous solution from a solution dispenser so as to contact the powder bed, thereby forming a solution-impregnated humid material;
  maintaining the solution-impregnated humid material supported by the surface and in substantially shear-less conditions until the solution-impregnated humid material agglomerates to produce an agglomerated humid material; and
  drying the agglomerated humid material thereby obtaining a dried agglomerated material; and
  grinding the dried agglomerated material thereby forming the water-absorbing material.

In some implementations, there is provided a process for manufacturing a water-absorbing material, comprising:
  providing an absorptive powder comprising a water-absorbing polysaccharide onto a surface, thereby obtaining a powder bed;
  releasing an aqueous solution from a solution dispenser so as to contact the powder bed, thereby forming a solution-impregnated humid material;
  maintaining the solution-impregnated humid material supported by the surface and in substantially shear-less conditions until the solution-impregnated humid material agglomerates to produce an agglomerated humid material; and
  drying the agglomerated humid material thereby obtaining a dried agglomerated material; and
  sieving the dried agglomerated material thereby forming the water-absorbing material.

In some implementations, there is provided a process for manufacturing a water-absorbing material, comprising:
  providing an absorptive powder comprising a water-absorbing polysaccharide onto a surface, thereby obtaining a powder bed;

releasing an aqueous solution from a solution dispenser so as to contact the powder bed, thereby forming a solution-impregnated humid material;

maintaining the solution-impregnated humid material supported by the surface and in substantially shear-less conditions until the solution-impregnated humid material agglomerates to produce an agglomerated humid material; and drying the agglomerated humid material thereby obtaining a dried agglomerated material; and grinding and sieving the dried agglomerated material thereby forming the water-absorbing material.

In some implementations, there is provided a process for manufacturing a chromogenic absorbent material, comprising:

providing an absorptive powder comprising a water-absorbing polysaccharide onto a surface, thereby obtaining a powder bed;

releasing a chromogenic aqueous solution from a solution dispenser so as to contact the powder bed, thereby forming a solution-impregnated humid material;

maintaining the solution-impregnated humid material supported by the surface and in substantially shear-less conditions until the solution-impregnated humid material agglomerates to produce an agglomerated humid material; and drying the agglomerated humid material thereby forming the chromogenic absorbent material.

In some implementations, there is provided a method for detecting a detectable substance in a medium, comprising:

exposing a chromogenic absorbent material to the medium, the chromogenic absorbent material comprising a trigger agent and a chromogenic indicator convertible into a chromogenically active substance in the presence of the trigger agent and the detectable substance; and monitoring the presence of the chromogenically active substance.

In some implementations, there is provided a method for detecting a detectable substance in a medium, comprising:

exposing a water-absorbing material to the medium;

contacting a chromogenic solution with the water-absorbing material after exposure to the medium, the chromogenic solution comprising a trigger agent and a chromogenic indicator convertible into a chromogenically active substance in the presence of the trigger agent and the detectable substance; and monitoring the presence of the chromogenically active substance.

In some implementations, contacting the chromogenic solution with the water-absorbing material comprises at least one of:

vaporizing the chromogenic solution onto the water-absorbing material;

pouring the chromogenic solution onto the water-absorbing material;

dripping the chromogenic solution onto the water-absorbing material; and soaking the water-absorbing material into the chromogenic solution.

DETAILED DESCRIPTION

Figure 1:
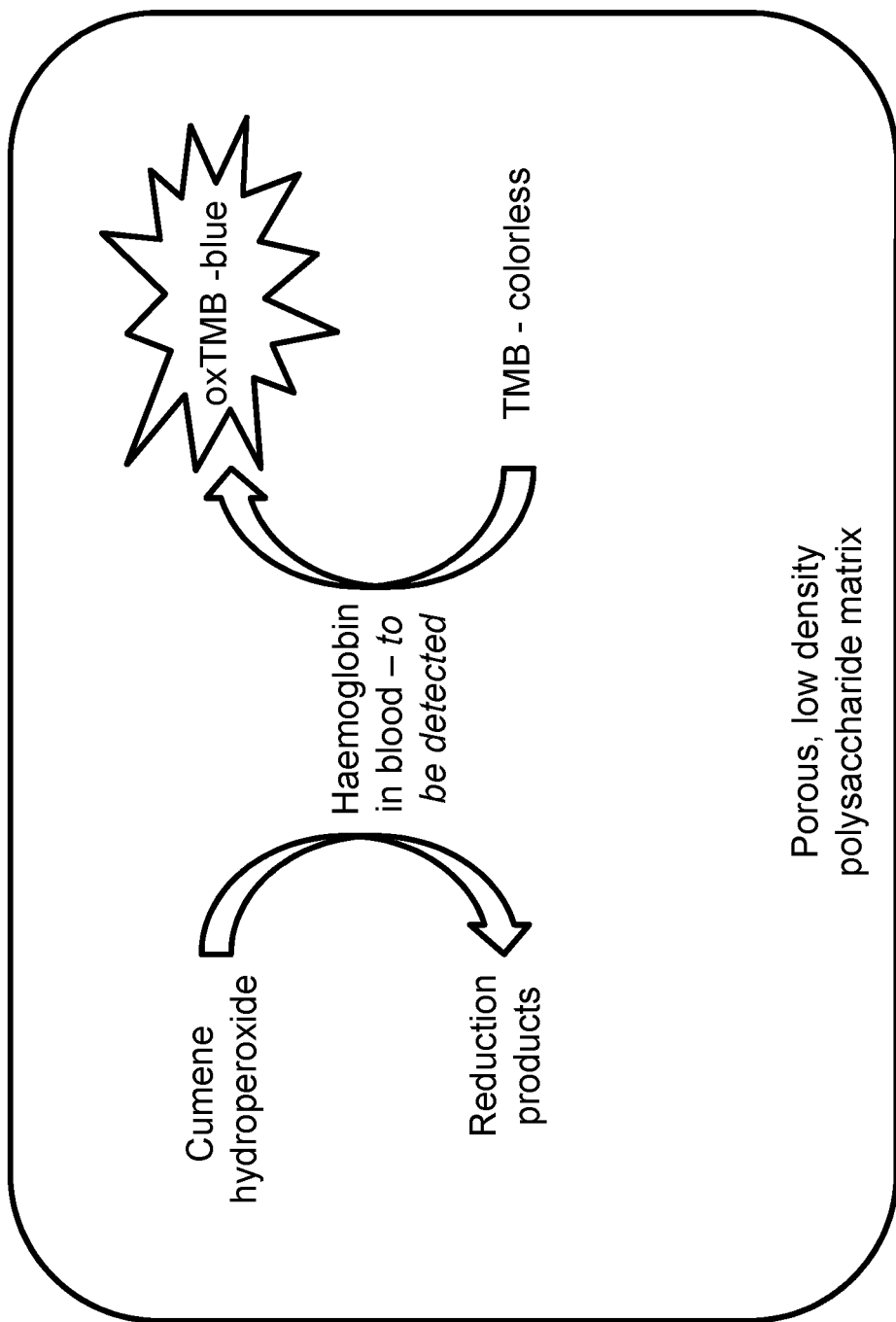
FIG. 1 is a scheme of the reaction pathway taking place in the particles of chromogenic absorbent material for the detection of blood in animal excretions.

The techniques described herein relate to a water-absorbing material, a process and system for manufacturing the water-absorbing material, and the use of the water-absorbing material for the detection of chemical species.

In some implementations, the process for manufacturing the water-absorbing material includes providing an absorptive powder including a water-absorbing polysaccharide onto a surface, thereby obtaining a powder bed; releasing an aqueous solution from a solution dispenser so as to contact the powder bed, thereby forming a solution-impregnated humid material; maintaining the solution-impregnated humid material supported by the surface and in substantially shear-less conditions until the solution-impregnated humid material agglomerates to produce an agglomerated humid material; and drying the agglomerated humid material, thereby forming the water-absorbing material.

It should be understood that the term "water-absorbing material" generally refers to a material which can absorb and retain aqueous liquids (i.e., water-containing liquids). The water-absorbing material can include saccharides, polysaccharides, synthetic absorbent polymers, clays, or combinations thereof. In some implementations, the water-absorbing material is produced in the form of particles of water-absorbing material.

Further, some implementations described herein include a process for manufacturing a chromogenic water-absorbing material for detecting diseases or conditions, such as diseases or conditions related to the presence of blood in animal excretions, (e.g. urinary tract disease, hemorrhage or cancer) or diseases related to higher-than-normal levels of glucose in the animal excretions (e.g. diabetes). It is understood that other diseases or conditions can be detected, as will be explained in further detail below.

It should be understood that the term "particles" refers to discrete pieces of material of various shapes obtained by the manufacturing process. Optionally, the particles may generally have a circular cross-section with an average diameter ranging from 2.5 mm to 10 mm. Optionally, the particles include granules.

Some implementations of the process and system are described in greater detail below.

Process for Manufacturing Water-Absorbing Material

As described herein, the water-absorbing material can be produced in the form of particles of water-absorbing material. However, it will be understood that the water-absorbing material can also be produced in other forms such as two-dimensional or one-dimensional structures. A non-limitative example of a two-dimensional structure includes a continuous sheet of water-absorbing material, optionally having a length and width of at least several cm and a thickness between 2.5 mm and 10 mm. a non-limitative example of a one-dimensional structure includes generally elongated structures such as an elongated cylinder, optionally having a length of at least several cm and a diameter between 2.5 mm and 10 mm. In some implementations, the one-dimensional and two-dimensional structures can optionally be cut or grinded to obtain particles of water-absorbing material. In some implementations, the water-absorbing material can be subjected to a size-reduction step (e.g. grinding step) and/or to a fractionation step (e.g. sieving step) in order to obtain particles of water-absorbing material having a certain particle size. In some implementations the water-absorbing material can be grinded and/or sieved in order to obtain particles of water-absorbing material having a certain particle size. For example, particles of water-absorbing material can be grinded and sieved over mesh screens of various sizes, including 12 mesh, 20 mesh, 80 mesh, 60 mesh and 100 mesh screens. It is understood that the different sizes of particles of water-absorbing material may be suited for various applications.

The composition of the absorptive powder and/or of the aqueous solution is chosen depending on the application and use of the particles of water-absorbing material, or to obtain certain desirable physical-chemical properties. For example, by controlling the operating parameters of the process, the composition of the absorptive powder and/or the composition of the aqueous solution, the particles of water-absorbing material can have a lower density and/or higher porosity than other absorbing particles manufactured by known processes such as wet granulation or extrusion. Further, some compositions of the absorptive powder allow for the solution-impregnated humid material to agglomerate more easily, for example without the need of mixing the solution-impregnated humid material or subjecting the solution-impregnated humid material to shear, after contact with the aqueous solution.

The process for manufacturing particles of water-absorbing material includes providing an absorptive powder onto a surface, thereby forming a powder bed. The absorptive powder can include at least one of the water-absorbing components of the water-absorbing material, for example a polysaccharide or other water-absorbing compounds in powder form or a mixture of several polysaccharides or other water-absorbing compounds in powder form.

The surface can be any suitable two-dimensional structure onto which the absorptive powder can be disposed. The surface can be curved or substantially planar. In some implementations, the surface is a substantially planar surface which can be horizontal or inclined. It is understood that by "substantially planar", it is meant that the surface is generally flat and in a plane, although there can be minor surface roughness to the surface. For example the substantially planar surface can include a table top, a working surface of a laboratory bench, a working surface of a fume-hood, or a top surface of a conveyor belt or other types of conveyors. It is understood that the surface may be immobile or mobile. A mobile surface may be in motion continuously or during certain time periods only. In some implementations, the powder bed is provided on the surface with a thickness D between about 0.5 cm and about 5 cm, or between 1 cm and 2 cm.

The process also includes releasing an aqueous solution from a solution dispenser so as to contact the powder bed, thereby forming a solution-impregnated humid material. It is understood that the solution-impregnated humid material corresponds to the amount of absorptive powder of the powder bed which has been contacted with the aqueous solution, and which has not yet been agglomerated into agglomerated humid material or agglomerated humid particles.

It is understood that the expression "aqueous solution" refers to a solution in which the solvent includes water. For example, and without being limitative, the aqueous solution can include water and other water-miscible solvents such as acetone, ethanol, methanol and/or isopropanol. For example, the aqueous solution can include mixtures of water and acetone, water and ethanol or water and isopropanol. It is also understood that the aqueous solution can include other compounds, such as chemically active compounds or pharmaceutically active compounds. In some implementations, the solvent includes at least 50 wt % water. In some implementations, the other compounds can include a chromogenic indicator and/or an oxidizing agent, as will be described in further detail below.

In some implementations, releasing the aqueous solution includes pouring the aqueous solution under gravity onto the powder bed. Pouring the aqueous solution can be performed, for example, by pouring a continuous flow of aqueous solution onto the powder bed, spraying the aqueous solution onto the powder bed (i.e., under pressure), or by dripping the aqueous solution in the form of discrete drops. For example, when pouring the aqueous solution includes dripping the aqueous solution in the form of discrete drops onto the powder bed, the agglomerated humid material is produced in the form of agglomerated humid particles.

The aqueous solution can be released onto the powder bed from a distance. The distance is selected to be sufficient enough to enable penetration of the aqueous solution into the powder bed without substantially displacing the powder bed. In the case that the aqueous solution is released by dripping the aqueous solution in the form of discrete drops, the distance can be selected such that an impact between the drops and the powder bed minimizes bursting of the drops and minimizes production of micro-drops which can contaminate the powder bed. For example, in some implementations this distance may be of at most 10 cm above the powder bed, for example between 5 cm and 10 cm above the powder bed, or such that the aqueous solution has a velocity of at most 1.5 m/s, or between 1 m/s and 1.5 m/s, upon contacting the powder bed.

Optionally, dripping the aqueous solution can be performed so that each drop of the aqueous solution contacts the powder bed at a different location. Optionally, dripping the aqueous solution can be performed so that each drop of the aqueous solution contacting the powder bed forms a corresponding solution-impregnated humid particle. In some implementations, the process includes handling the solution-impregnated humid particles to remain isolated from each other until the solution-impregnated humid particles agglomerate, thereby forming respective agglomerated humid particles.

In some implementations, the process includes maintaining the solution-impregnated humid material supported by the surface and in substantially shear-less conditions until the solution-impregnated humid material agglomerates to produce an agglomerated humid material. In other words, after contact of the powder bed with the aqueous solution, the solution-impregnated humid material is kept in contact with the surface and in substantially shear-less conditions (or very low shear conditions) until an agglomerated material is produced. It is understood that the solution-impregnated humid material being "supported by the surface" or "kept in contact with the surface" means that the solution-impregnated humid material can either be directly supported by (or in direct contact with) the surface or indirectly supported by the surface through an underlying part of the powder bed which has not been contacted with the aqueous solution.

In some implementations, the powder bed is provided with a thickness D which prevents the solution from going through the powder bed and come into direct contact with the surface. In other words, the powder bed and the solution can be contacted such that the solution-impregnated humid material remains in spaced relation with respect to the surface—in such case, it is understood that the solution-impregnated humid material is indirectly supported by the surface through the underlying part of the powder bed, as explained herein. It is also understood that the material supported by the surface can be substantially immobile relative to the surface or can be moving relative to the surface.

It is understood that by "substantially shear-less" or "very low shear" conditions, it is meant that the solution-impregnated humid material is not subjected to shearing forces strong enough to cause a mechanical deformation of the solution-impregnated humid material. For example, the absorptive powder and the aqueous solution are not mechanically mixed or extruded. It is also understood that the shearing forces caused by optional conveying of the solution-impregnated humid material on a conveyor belt or other types of conveyors is considered to be negligible, such that the displacement of the solution-impregnated humid material on a conveyor during agglomeration is considered within the scope of the expression "substantially shear-less conditions".

It is understood that the term "agglomeration" (or corresponding verb "to agglomerate") refer to the aggregation of the solution-impregnated humid material in order to gather, form or crystallize into a ball, mass, cluster or a larger aggregate (i.e., grains or granules). The agglomeration is caused by the wetting of the powder bed by the aqueous solution (also referred to as an agglomeration liquid) and subsequent adhesion of particles of wetted powder (i.e, the solution-impregnated humid material) together in order to form the ball, mass, cluster or larger aggregate (i.e., the agglomerated humid material). The agglomeration of the solution-impregnated humid material to produce the agglomerated humid material can take an agglomeration period between 1 second and several minutes (e.g., 2 or 3 minutes), or between several seconds (e.g., 5 or 10 seconds) and 1 minute, depending on the composition of the absorptive powder and the aqueous solution. It is understood that during the agglomeration period, the solution-impregnated humid material can be displaced on the surface or kept substantially immobile relative to the surface.

The process also includes drying the agglomerated humid material, thereby forming the particles of water-absorbing material. In some implementations, the drying is performed under vacuum. In some implementations, the drying is performed by heating at temperatures ranging from ambient temperature to about 65° C. The drying can for example be performed in a drying oven or a rotary evaporator.

Optionally, the process can further include displacing the solution-impregnated humid material away from the solution dispenser, for example on a conveyor belt. The solution-impregnated humid material can be in translation relative to the solution dispenser. Typically, the powder bed passes below the solution dispenser, but other configurations are possible.

Optionally, the aqueous solution can be released to contact part of the absorptive powder to form the agglomerated humid material, while another part of the absorptive powder can remain as residual powder. The residual powder can be separated from the agglomerated humid material, for example by sieving, and at least a portion of the residual powder can be recycled to form part of the powder bed.

In some implementations, the particles of water-absorbing material can be grinded in order to reduce their size and/or to increase the surface area contactable with a water-containing medium for absorbing all or part of the water thereof. The grinding can be performed using a grinder which is suitable to grind the particles of water-absorbing material depending on their composition. Example of grinders which may be used depending on the composition of the water-absorbing material include but are not limited to belt grinders, bench grinders, cylindrical grinders, surface grinders, tool grinders, jig grinders, gear grinders, die grinders or combinations thereof. In some implementations, the particles of water-absorbing material can be sieved (either directly or after a grinding step) in order to separate the particles of water-absorbing material according to their particle size.

The composition of the absorptive powder is selected such that the agglomeration can take place in substantially shear-less conditions, as explained herein. To such end, the absorptive powder includes a water-absorbing polysaccharide. The water-absorbing polysaccharide provides absorptive properties to the water-absorbing material. In some implementations, the water-absorbing polysaccharide may be a starch, a modified starch, amylopectin, amylose, modified amylose, a cellulose derivative, an alginate, an alginate derivative, a gelling polysaccharide or a mixture thereof. Non-limiting examples of starches and modified starches are starch granules, pregelatinized starch, waxy starches, anionic starches, cationic starches, fractionated starches, cross-linked starches or mixtures thereof. Such starches may be obtained from many sources, including but not limited to wheat, maize, buckwheat, potato, cassava, sorghum, millet, oat, arrowroot, barley, beans, peas, rice, rye, and mixtures thereof. Non-limiting examples of cellulose derivatives are cellulose esters and cellulose ethers, or a mixture thereof. A non-limiting example of a cellulose ether is carboxymethyl cellulose (CMC). Non-limiting examples of gelling polysaccharides are agar-agar, guar and xanthan, or a mixture thereof.

Optionally, the water-absorbing polysaccharide can be a glass-like polysaccharide. Glass-like polysaccharides are substantially amorphous polysaccharides and include glass-like characteristics. Glass-like polysaccharides substantially lack an organized crystalline pattern. Glass-like polysaccharides are typically prepared by melting or heating the polysaccharide to a temperature above its glass-transition temperature, followed by cooling to a temperature below its glass transition or melting point temperature. A non-limiting example of a glass-like polysaccharide, which has been found to be particularly suitable to be included in some implementations of the absorptive powder is pregelatinized starch.

Optionally, the absorptive material further includes a superabsorbent polymer (SAP). Optionally, the absorptive material includes in weight up to about 3 wt. %, or between 1 wt. % and 2.5 wt. % of the SAP. Non-limiting examples of SAP are poly(acrylic acids) and poly(methacrylic acids), salts thereof, or mixtures thereof. A non-limiting example of SAP is sodium polyacrylate, which is an efficient SAP. It should be understood that other types of SAPs may be used, such as superabsorbent starches or other synthetic superabsorbent polymers.

In an optional aspect, each particle of water-absorbing material further includes a second polysaccharide providing structural integrity. By "providing structural integrity", it is meant that the second polysaccharide reduces or prevents the breaking up of the particles of water-absorbing material upon handling or upon contact an aqueous liquid. In other words, the second polysaccharide reduces the brittleness of the water-absorbing material while preventing an increase of the softness or pliability of the water-absorbing material. In some scenarios, the second polysaccharide provides sufficient structural integrity so that the particles of the water-absorbing material cannot be easily broken or fractured by hand and are relatively unpliable and rigid. For example, when the absorptive material consists of 100 wt % pregelatinized starch, the particles of water-absorbing material can tend to be soft and pliable and thus not as easily manipulated.

Optionally, the second polysaccharide includes a crystalline polysaccharide. Examples of crystalline polysaccharides are cellulose, cellulose derivatives or mixtures thereof. In an optional aspect, the cellulose includes microcrystalline cellulose (MCC), nanocrystalline cellulose (NCC) or a mixture thereof. In an optional aspect, the absorptive material includes in weight: about 35% to about 65% or about 45% to 55% of the water-absorbing polysaccharide, and about 35% to about 65% or about 45% to about 55% of the second polysaccharide. In an optional aspect, the crystalline polysaccharide is less water-absorbent than the water-absorbing polysaccharide. When the absorptive powder includes more than one constituent, the process further includes mixing together the constituents (for example, the water-absorbing polysaccharide and the second polysaccharide), in order to form the absorptive powder.

In some implementations, depending on the composition of the absorptive powder, the particles of water-absorbing material may have a density of about 0.20 g/cm$^3$ to about 0.39 g/cm$^3$, of about 0.20 g/cm$^3$ to about 0.35 g/cm$^3$, of about 0.25 g/cm$^3$ to about 0.35 g/cm$^3$, or of about 0.30 g/cm$^3$ to about 0.35 g/cm$^3$.

In some implementations, depending on the composition of the absorptive powder, the chromogenic absorbent material may have a total porosity of about 65% to about 85%, or of about 70% to about 80%. It is understood that the total porosity refers to the fraction of the bulk material volume (V) which is not occupied by solid matter. If the volume of solids is denoted by Vs, and the pore volume as Vpore=V−Vs, the total porosity can be expressed as shown in Equation 1 below.

$$\text{total porosity} = \phi = \frac{V - Vs}{V} = \frac{Vpore}{V} (\text{mL/mL}) \quad \text{Equation 1}$$

The total porosity may for example be measured by: placing a known volume of particles of water-absorbing material into a container; covering the particles with a liquid; and measuring the volume of liquid needed to cover the particles (Vc). The total porosity is then expressed as the ratio of the volume of added liquid (Vc) to the volume of particles (V).

In some implementations, depending on the composition of the absorptive powder, the particles of water-absorbing material have an effective porosity of about 0.5 mL/g to about 2.0 mL/g, of about 0.6 mL/g to about 1.5 mL/g, of about 0.8 mL/g to about 1.2 mL/g or of about 0.9 mL/g to about 1.1 mL/g. It is understood that the effective porosity (also referred to as connected porosity or true porosity) is defined as the ratio of the connected pore volume to the total bulk volume. The effective porosity may for example be measured by: placing a known mass (m) of particles of water-absorbing material into a container; covering the particles with a liquid; measuring the volume of liquid needed to cover the particles (Vc); removing the soaked particles from the container; measuring the liquid remaining in the container (Vr); and calculating the volume of liquid absorbed in the chromogenic absorbent particles (Va=Vc−Vr). The effective porosity may then be obtained as shown in Equation 2 below.

$$\text{effective porosity} = \phi_e = \frac{Vc - Vr}{m} = \frac{Va}{m} (\text{ml/g}) \qquad \text{Equation 2}$$

It is to be noted that the effective porosity may also be expressed as the ratio Va/V in ml/ml.

In some implementations, the particles of water-absorbing material have a free swelling capacity (FSC) greater than about 900%, or greater than about 1000%. The FSC is one type of measurement used for measuring the absorption properties of a material. An FSC measurement is performed by soaking the material to be tested in a liquid to be absorbed (in the present case, water) for a given time and weighing the material after the liquid has been absorbed.

In some implementations, the particles of water-absorbing material have a hardness which is sufficient to withstand the weight of an animal (e.g. a cat or a dog) standing on the particles (i.e. a part of the animal's weight is applied onto the particle). In some implementations, the force required for compressing spheroidal particles of water-absorbing material having a mass between 22 mg and 38 mg by 1 mm is between about 15 N and about 90 N. It should be understood that the "hardness" of a particle of water-absorbing material refers to the ability of the particle to be deformed by applying a compression force onto the particle, without the particle breaking or disaggregating. It should also be understood that in some implementations, depending on the composition of the particles of water-absorbing material and conditions of agglomeration, less than about 20% of the particles break or are disaggregated after a compression of more than 1.1 mm.

System for Manufacturing Particles of Water-Absorbing Material

Figure 10:
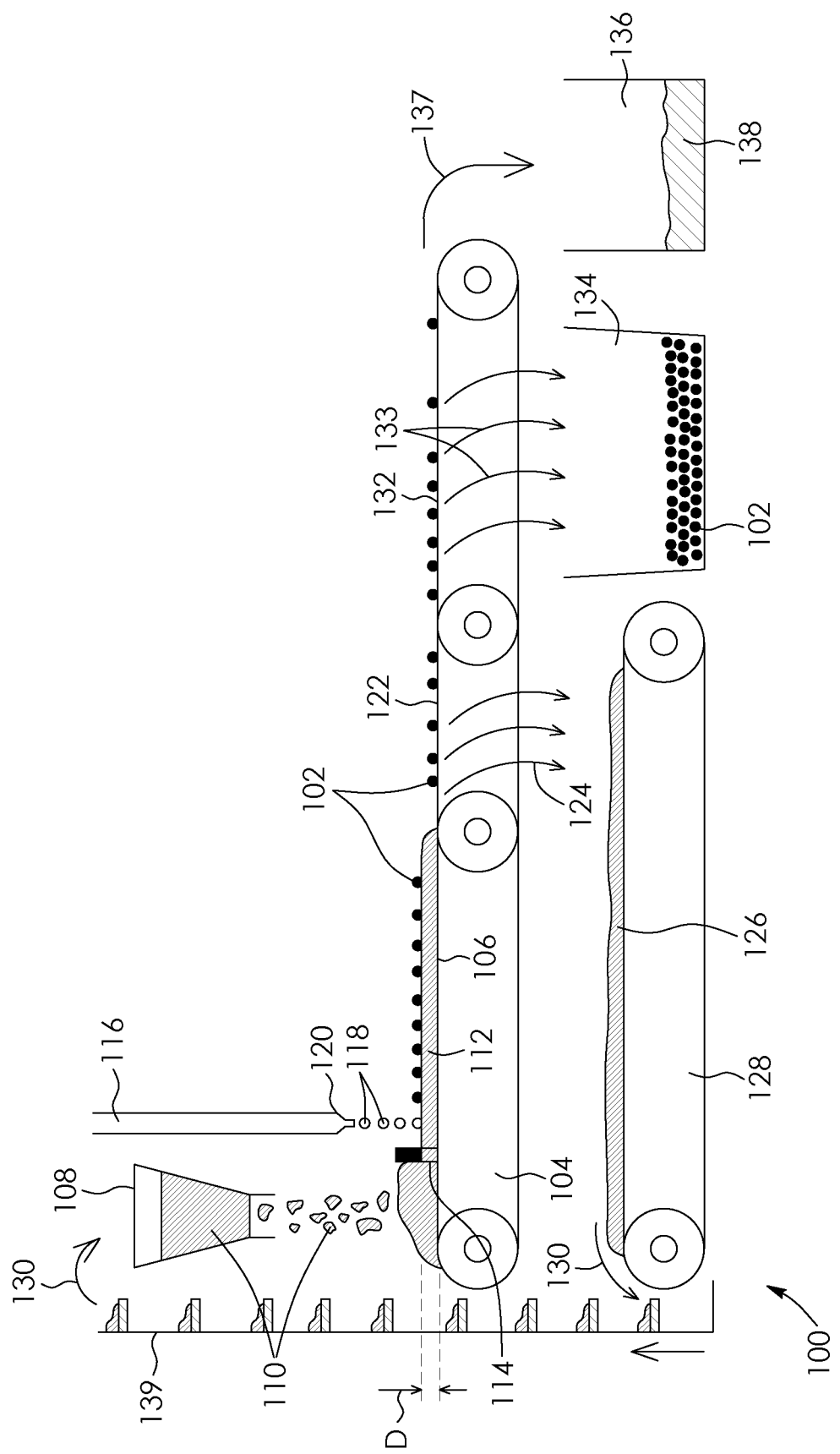
FIG. 10 shows a schematic representation of an apparatus used for the manufacturing of particles of water-absorbing material.

Now referring to FIG. 10, there is provided a system for manufacturing the particles of water-absorbing material. The system includes an apparatus 100 for forming the agglomerated humid material 102 and a dryer (not shown) for drying the agglomerated humid material and forming the particles of water-absorbing material. The apparatus 100 also includes a conveyor 104 including a conveying surface 106, which is in this case a substantially planar surface. In some implementations, the conveying surface 106 can be operated such that the particles of agglomerated humid material 102 are displaced at a speed between about 0.1 m/min to about 6 m/min, or between about 1.2 m/min to about 6 m/min.

The apparatus 100 also includes a powder feeder 108 located at a first end of the conveyor 104. The powder feeder 108 is used for disposing absorptive powder 110 onto the conveying surface 106, thereby forming a powder bed 112. In some implementations, the powder feeder 108 has a loading capacity of up to about 30 L of the absorptive powder 110.

In some implementations, the apparatus 100 can include a thickness controlling unit 114 for controlling a thickness D of the powder bed 112. The thickness controlling unit 114 can be located proximate to the powder feeder 108 and can optionally include a blade located above the conveying surface 106. In some implementations, the thickness controlling unit 114 is configured so that the thickness of the powder bed is between 0.5 cm and 5 cm, or between 1 cm and 2 cm.

The apparatus 100 also includes a solution supply (not shown) connected to a solution delivery unit 116. The solution delivery unit 116 is configured for releasing the aqueous solution onto the powder bed 112. Typically, the powder bed 112 passes below the solution delivery unit 116, but other configurations are possible. In some implementations, the solution delivery unit 116 is configured for dripping discrete drops 118 of the aqueous solution onto the powder bed 112, such that the drops 118 are impregnated with respective amounts of the absorptive powder, thereby forming the solution-impregnated humid material which agglomerates to form the agglomerated humid material 102. In other implementations, the solution delivery unit 116 is configured for spraying the aqueous solution onto the powder bed 112 or for pouring the aqueous solution onto the powder bed 112 in a sheet-like manner.

In some implementations, the solution delivery unit 116 includes at least one solution outlet 120 located at a height above the conveying surface 110. For example, solution outlet 120 can be located between 5 cm and 10 cm above the conveying surface 106. In some implementations, the solution delivery unit 118 includes a plurality of solution outlets 120 spaced from each other. Optionally, the solution outlets 120 span across the width of the conveying surface 106. For example, the solution delivery unit 116 can include ten solution outlets 120 spaced from each other by about 2 cm to 4 cm.

Still referring to FIG. 10, in some implementations, the apparatus 100 can include a first sieve 122 (i.e., a powder sieve) located on or embedded in the conveying surface 106, for retrieving 124 at least part of residual absorptive powder 126. The residual absorptive powder 126 is the remaining absorptive powder 110 which was not contacted by the aqueous solution released from the solution delivering system 116. Optionally, the apparatus 100 can further include a second conveyor 128 or a powder recycling bin (not shown) located under the first sieve 122, for receiving the residual absorptive powder 126. The residual absorptive powder received on the second conveyor 128 or in the powder recycling bin can be recycled back 130 to the powder feeder 108 and reused as absorptive powder 110. In some implementations, the residual absorptive powder 126 can be conveyed back to the powder feeder 108 using a vertical conveyer 139. In some implementations, the residual absorptive powder 126 can be manually recovered from the powder recycling bin and into the powder feeder 108. In some implementations, the apparatus 100 can include a second sieve 132 (i.e., a particle sieve) located on or embedded in the conveying surface 106, for recovering 133 the agglomerated humid material 102. Optionally, the apparatus 100 can further include an agglomerated humid material recovery bin 134 located under the second sieve 132, for receiving the agglomerated humid material 102. In some implementations, the apparatus 100 can include a waste material recovery bin 136, for recovering 137 waste material 138 which was not sieved by the first and second sieves 122, 132. In some implementations, the perforations of the first sieve 122 are of about 3.5 mm to about 4 mm. In some implementations, the perforations of the second sieve 132 are of about 4.5 mm to about 5 mm.

It is understood that the length of the conveying surface 106 and the speed at which the conveying surface is displaced can vary depending on the time required for the agglomerated humid material to be formed. The length of the conveying surface 106 and the displacement speed of the conveying surface 106 can therefore be adapted such that the agglomerated humid particles are recovered 133 shortly after they are formed. In some scenarios, optimizing the length and displacement speed of the conveying surface 106 can allow for reduced energy consumption of the system.

Particles of Chromogenic Absorbent Material for Use in Animal Litter and Process for Manufacturing the Same The process described herein can for example be used for manufacturing additives to be used in or in conjunction with an animal litter. This exemplary application more specifically relates to a process of manufacturing a chromogenic water-absorbing material which may be used for detecting diseases or abnormalities in excretions (also referred to herein as a "chromogenic absorbent material") for detecting diseases such as urinary tract disease, hemorrhage, cancer or diabetes in animal excretions.

In some implementations, the chromogenic absorbent material includes a chromogenic indicator and an absorptive powder (as described herein and also referred to herein as an "absorptive material"). In some implementations, the chromogenic absorbent material further includes an oxidizing agent. The chromogenic absorbent material can allow detecting disease features when contacted with excretions and/or abnormalities in the excretions. In some implementations, the chromogenic absorbent material is provided for detecting blood in excretions. In some implementations, the chromogenic absorbent material is provided for detecting glucose in excretions. In some implementations, the chromogenic absorbent material is provided for measuring the pH of excretions. In some implementations, the chromogenic absorbent material may be used in connection with an animal litter.

It should be understood that excretion refers to any matter excreted by an animal, such as urine or fecal matter. The chromogenic absorbent material may be used in any domestic animal litter including cat litter, dog litter (such as puppy pads) and rodent litter. It may also be used for horse litter, cow litter or any other livestock litter. However, various implementations of the chromogenic absorbent material are not limited to detecting blood or glucose in animal excretions, or measuring the pH of animal excretions, and may be used to detect blood or glucose in human excretions, or for measuring the pH of human excretions, for example.

Particles of the chromogenic absorbent material may be dispersed within the animal litter or at the surface of the animal litter. In some implementations, the particles of the chromogenic absorbent material have a density which is lower than the density of the particles of the animal litter, such that the particles of the chromogenic absorbent material migrate to the surface of the animal litter when the animal litter is shaken. The animal litter may include clay based particles, cellulosic particles, perlite based particles, silica based particles, corn based particles, paper based particles, wheat based particles or other organic-based litter particles, or a combination thereof. For example and without being limitative, clay based particles may include bentonite and/or montmorillonite.

It is understood that the term "animal litter" refers to the absorbent material which is capable of absorbing water present in the animal excretions. It is understood that the particles of chromogenic absorbent material can be used directly as an animal litter, or as additives to the animal litter. In the case of cats, it is understood that the term "animal litter" may refer to any commercially available cat litter or a similar cat litter, including clay-based (such as bentonite-based) cat litter or biodegradable cat litter. In the case of dogs, it is understood that the term "animal litter" may refer to the absorbent material (such as superabsorbent polymers) which may be used in puppy pads, or any absorbent material which may be directly used for absorbing dog excretions.

In some implementations, the animal litter is cat litter, and the absorbent material can be deposited in the cat litter as an additive thereto. In some implementations, the particles of chromogenic absorbent material are small enough to be unnoticed by the cat using the litter, but large enough so that the cat's owner can visually detect a color change.

In some implementations, the animal litter is dog litter, such as the absorbent material of a puppy pad. Alternatively, the absorbent material can be used in a diaper, such as a diaper for babies or for the elderly. Puppy pads and diapers are typically formed of a plurality of layers, which include at least one absorbent layer or several absorbent layers. For example, a diaper can include a topsheet layer in contact with the skin, a distribution layer under the topsheet which moves the liquid away from the skin and an absorbent core which may contain superabsorbent polymers for absorbing most of the liquid from the excretion. Similarly, a puppy pad can include a first non-woven layer, a tissue sheet to structurally hold the other layers in place, and at least one absorbent layer which may include superabsorbent polymer. It is understood that the chromogenic absorbent material described herein may be incorporated into a diaper or a puppy pad between any of the layers.

In some implementations, the chromogenic absorbent material can be incorporated between the first layer (the layer in contact with the skin in the diaper, or the topsheet of the puppy pad), and the second layer so that visual detection of the color change is more convenient. In some implementations, the chromogenic absorbent material can be incorporated with the superabsorbent polymer (i.e., in one of the layers of superabsorbent polymer). In some implementations, the chromogenic absorbent material can be incorporated in the last layer of the structure (diaper or puppy pad) and the exterior of the structure can be made of a transparent material so that visual detection is convenient. In some implementations, the chromogenic absorbent material is disposed in a line at the center of the structure (longitudinally or laterally), under the first layer.

In some implementations, the particle size of the chromogenic absorbent material is reduced by grinding and/or sieving prior to being incorporated into the structure. For example, the particles of chromogenic absorbent material can be grinded and/or sieved so that the particle size is less than 12 mesh to 100 mesh for diapers, and less than 8 mesh to 60 mesh for puppy pads.

In some implementations, the particles of chromogenic absorbent material include: an oxidizing agent responsive to peroxidatic/pseudoperoxidatic activity in an excretion to provide oxidizing activity, or a first catalytic compound generating the oxidizing agent in situ; a chromogenic indicator being chromogenically responsive to the oxidizing activity of the oxidizing agent; and an absorptive material for absorbing the excretion, the absorptive material including a water-absorbing polysaccharide providing absorptive properties to the chromogenic absorbent material.

It should be understood that the expression "peroxidatic activity" refers to the ability of catalytic compounds to drive the reaction between hydroperoxides and colorless chromogenic electron donors which become fluorescent or visibly colored after oxidation.

It should be understood that the expression "pseudoperoxidatic activity" refers to the ability of a peroxidase or a non-peroxidase catalytic compound to drive the reaction between hydroperoxidases and colorless chromogenic electron donors which become fluorescent or visibly colored after oxidation. Certain transition metals and their ions and hemoproteins are known to have pseudoperoxidatic activity. Basophils, neutrophils, eosinophils and mast cells synthesize endogenous peroxidase which can be visualized at the ultrastructural level in the secretory apparatus of immature cells. Red blood cells and hematin containing compounds have iron as part of their heme groups, which can catalyze the oxidation of chromogenic electron donors. This pseudoperoxidatic activity can be inhibited with strong $H_2O_2$ solutions, sodium azide and methanol-$H_2O_2$ solutions.

The oxidizing agent is reactive to peroxidatic/pseudoperoxidatic activity and is able to oxidize the chromogenic indicator in the presence of a peroxidase or a pseudoperoxidase. For example, the peroxidase can be horseradish peroxidase. For example, the pseudoperoxidase can be haemoglobin present in blood. In an optional aspect, the oxidizing agent includes a hydroperoxide.

It should be understood that "hydroperoxide" refers to compounds of the general formula ROOH, wherein the R group is an aryl, alkyl or acyl group (organic hydroperoxide), or a hydrogen atom (hydrogen peroxide). For example and without being limitative, the hydroperoxide can be cumene hydroperoxide (CHP), diisopropylbenzene dihydroperoxide or hydrogen peroxide, or a mixture thereof. Hydroperoxides are suitable for the detection of peroxidatic/pseudoperoxidatic activity.

In some implementations, the oxidizing agent may be a hydroperoxide precursor such as sodium percarbonate. Sodium percarbonate is a chemical adduct of sodium carbonate and hydrogen peroxide. The formula of sodium percarbonate is $2Na_2CO_3.3H_2O_2$. Sodium percarbonate decomposes to sodium carbonate and hydrogen peroxide, for example upon contact with water.

In some implementations, the oxidizing agent is not initially added to the chromogenic absorbent material, but is generated in situ by a first catalytic compound present in the chromogenic absorbent material. It should be understood that "generated in situ" means that the oxidizing agent is directly synthesized in the chromogenic absorbent material from a precursor. For example, the first catalytic compound may be an enzyme such as an oxido-reductase. For example, the first catalytic compound may be glucose oxidase (GOx). Optionally, the precursor may be oxygen ($O_2$), which can be reduced to hydrogen peroxide in the presence of glucose oxidase. In an optional aspect, the reduction of the precursor to the oxidizing agent can take place in the presence of a saccharide or polysaccharide which can be oxidized by the first catalytic compound.

In some implementations, the oxidizing activity of the oxidizing agent is triggered by the presence of peroxidatic/pseudoperoxidatic activity in excretions. The oxidizing agent therefore oxidizes the chromogenic indicator which then changes of color. More particularly, the chromogenic indicator is an electron donor, i.e. a reducing agent that changes color upon losing an electron.

In some implementations, the chromogenic indicator is a benzidine-type compound, i.e. a compound as shown in formula I:

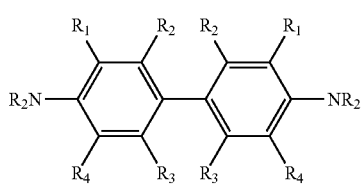

Formula I

In Formula I, groups $R_1$, $R_2$, $R_3$ and $R_4$ may be the same or different and may be hydrogen, halogen, a lower alkyl or alkoxy group containing 1 to 4 carbon atoms, a ($C_1$-$C_4$)-dialkylamino group, an acetylamino group, a nitro group or an aromatic group which may be substituted.

Optionally, the chromogenic indicator may be a compound as shown in Formula II:

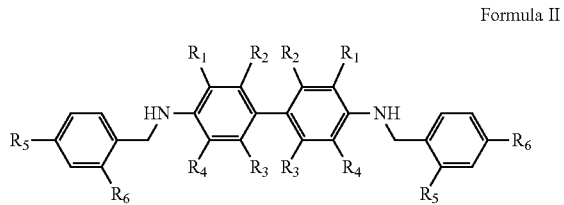

Formula II

In Formula II, groups $R_1$, $R_2$, $R_3$ and $R_4$ may be the same or different and represent hydrogen, halogen, and a lower alkyl or alkoxy group containing 1 to 4 carbon atoms, a ($C_1$-$C_4$)-dialkylamino group, an acetylamino group, a nitro group or an aromatic group which may be substituted; $R_5$ and $R_6$ are the same or different and represent water-soluble groups as hydroxyl group, amino group, acidic group, disulfonyl group, ether group, halogen, and a lower alkyl or alkoxy group containing 1 to 4 carbon atoms, a ($C_1$-$C_4$)-dialkylamino group, an acetylamino group or a nitro group.

Thus, a water soluble benzidine-type chromogenic indicator of Formula II, responds in the presence of hydroperoxide and peroxidase by changing its light absorptive capability, which is due to the chemical transformation to the compound shown in Formula III:

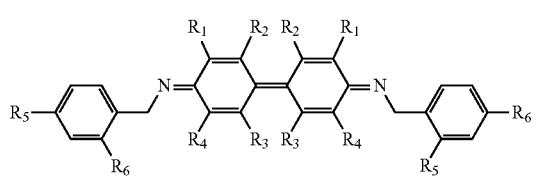

Formula III

It is understood that several different types of benzidine chromogenic indicators may be used.

Optionally, the chromogenic indicator may be 3,3',5,5'-tetramethylbenzidine (TMB). TMB is a colorless agent which turns blue upon oxidation. The peroxidase and/or pseudo-peroxidase catalyze the oxidation of TMB by the oxidizing agent (hydroperoxide) according to the following oxidation reaction.

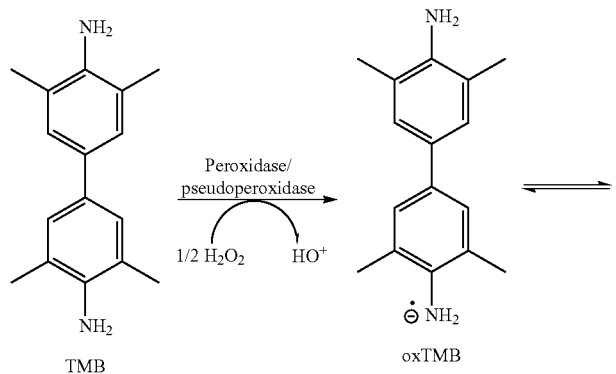
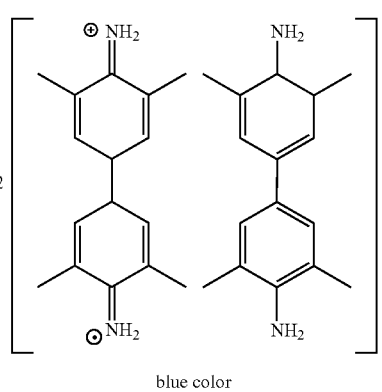

In some implementations, the chromogenic absorbent material may turn blue upon contact with excretions containing at least traces of blood (with therefore peroxidase/pseudo-peroxidase activity).

It should be understood that "blue" refers to any shade of blue. The chromogenic absorbent material may need a contact time with excretions sufficient to enable coloration. In an optional aspect, the particles may turn blue after a contact time ranging from about 10 seconds to about 30 min, or from about 10 seconds to about 1 min, depending on the nature of the absorptive material.

In some implementations, the chromogenic absorbent material may turn to different shades of blue depending on the blood or glucose concentration in excretions. The intensity of the blue shade may be proportional to the blood concentration or glucose concentration in excretions.

In some implementations, the chromogenic absorbent material may include an odor-retardant agent. For example, the odor-retardant agent may be N-(n-butyl) thiophosphoric triamide (n-BTPT), having the molecular formula $C_4H_{14}N_3PS$ with the following structure:

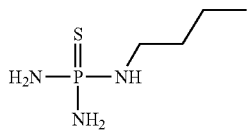

In some implementations, the chromogenic composition may further include a colour enhancer. Optionally, it may also include a buffering agent, a stabilizer, a metal scavenger agent or a combination thereof. The colour enhancer may optionally be 6-methoxyquinoline, lepidin, phenol derivatives, nitrobenzene, N-methylpyrrolidone, ethylene carbonate or any combination thereof. The buffering agent may optionally include citrate, sodium citrate, phosphate, acetate or any combination thereof. In some implementations, the buffering agent is used for maintaining the pH of the solution at about 5. The stabilizer may optionally be ascorbic acid, ammonium molybdate and derivatives thereof, polyethylene glycol, polyvinylpyrrolidone, polyethylene oxide and derivatives thereof, dibutylhydroxytoluene (BHT), or combination thereof. The metal-scavenger agent may optionally be EDTA, EDTA sodium salt or any combination thereof.

Figure 9:
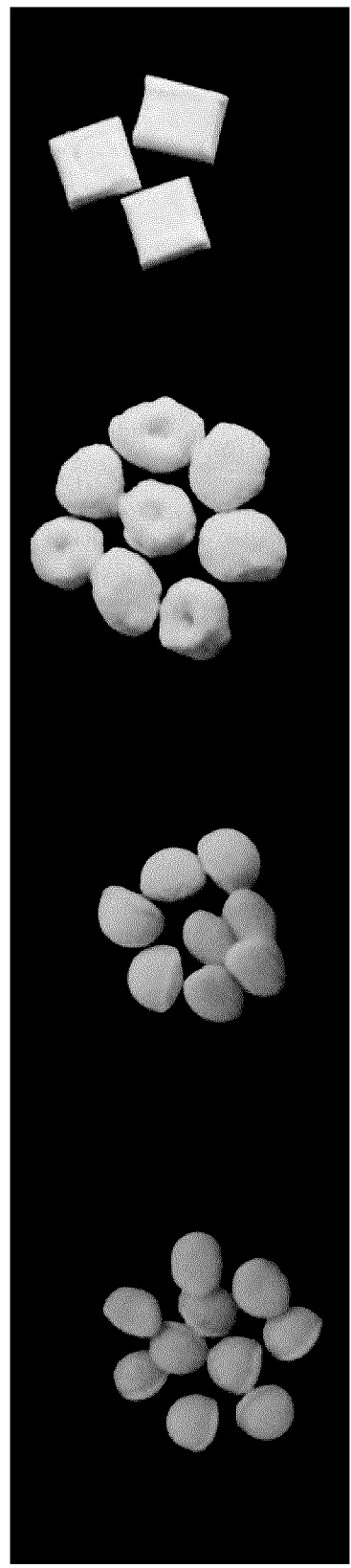
FIG. 9 shows photographs of extruded starch particles (9A, comparative), extruded starch particles in which gas was injected during extrusion (9B, comparative), particles of chromogenic absorbent material in which the absorptive material includes 50% PGS and 50% MCC (9C), and particles of pressed cellulose (9D, comparative).

Now referring to FIG. 9, a photograph showing different particles is shown. Particles 9A are extruded starch particles obtained under high shear, without injection of gas during extrusion. Particles 9A were made as a comparative example. Particles 9B are extruded starch particles obtained under high shear, with injection of gas during extrusion, Particles 9B were made as a comparative example. Particles 9D are pressed cellulose pulp particles and were also made as a comparative example. Particles 9C are chromogenic absorbent particles in which the absorptive material includes 50% pregelatinized starch (PGS) and 50% microcrystalline cellulose (MCC). Particles 9C were obtained through an implementation of the process as described herein and correspond to sample 25 as detailed in Example 2.

As can be seen in FIG. 9, particles 9A and 9B are in the form of compact pellets and particles 9D are in the form of pressed, compact squares. Particles 9C of chromogenic absorbent material (i.e. particles of water-absorbing material) are in the form of granules having a concave shape on one side and a convex shape on an opposite side.

Scanning electron micrographs of the particles of FIG. 9 were obtained in order to compare the morphology of particles 9A, 9B, 9C and 9D. Scanning electron micrographs showing the surface of the particles are shown in FIGS. 6A to 6D. Scanning electron micrographs showing cross sections of the particles are shown in FIGS. 7A to 7C and 8A to 8C. The scanning electron microscope used was a MEB JEOL JSM-5900LV™ (low vacuum).

Figure 6A:
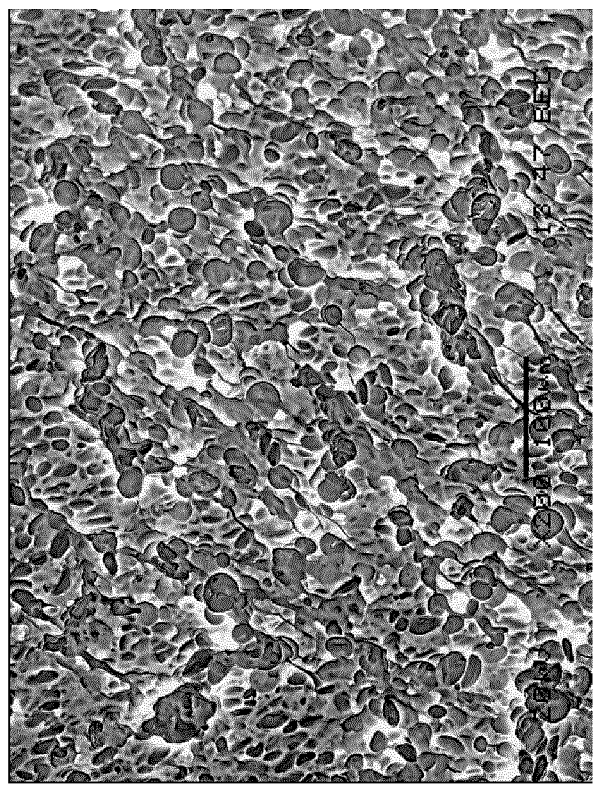
FIG. 6A is a ×200 scanning electron micrograph showing the surface of an extruded starch particle (comparative Figure).
Figure 6B:
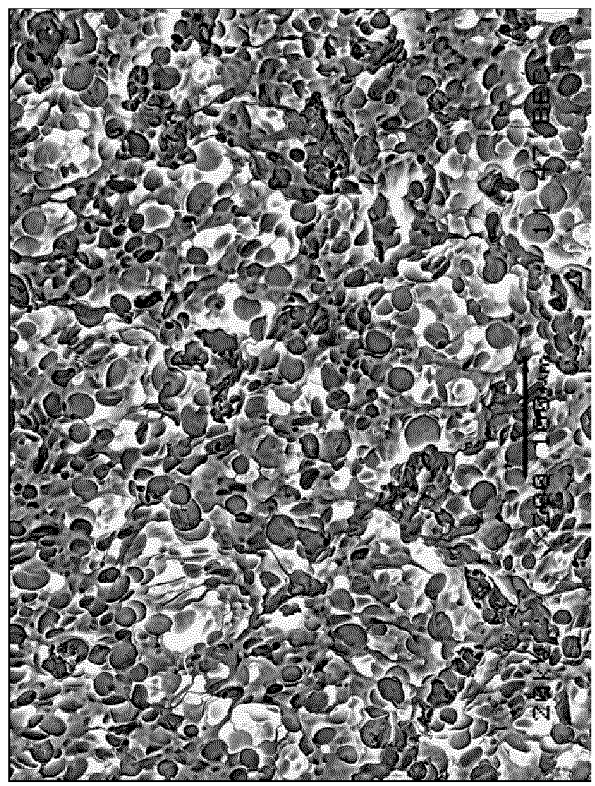
FIG. 6B is a ×200 scanning electron micrograph showing the surface of an extruded starch particle in which gas was injected during extrusion (comparative figure).

FIGS. 6A and 6B (comparative) show the surface of extruded starch particles obtained under high shear, with and without injected gas during extrusion. As can be seen, the surface of the extruded starch includes microscopic starch globules having a size of between about 5 μm and about 30 μm.

Figure 6D:
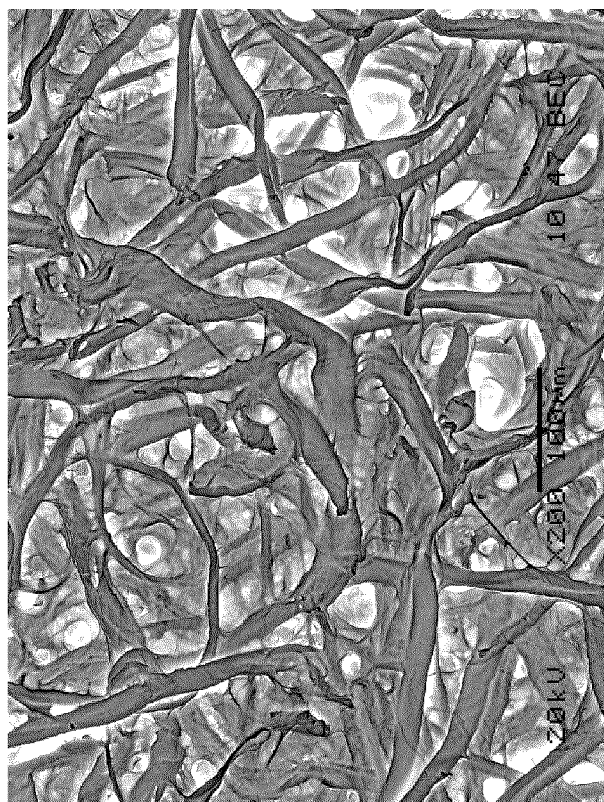
FIG. 6D is a ×200 scanning electron micrograph showing the surface of a particle of pressed cellulose (comparative figure).

FIG. 6D (comparative) shows the surface of pressed cellulose pulp particles. Elongated cellulose fibers can be seen on the surface. The fibers have a length of between about 100 μm and about 400 μm, and a width of between about 10 μm to about 30 μm.

Figure 6C:
FIG. 6C is a ×200 scanning electron micrograph showing the surface of a particle of chromogenic absorbent material in which the absorptive material includes 50% PGS and 50% MCC.

FIG. 6C shows the surface of chromogenic absorbent particles manufactured using an implementation of the process described herein, and in which the absorptive material includes 50% pregelatinized starch (PGS) and 50% microcrystalline cellulose (MCC). Microsructures of various shapes can be seen on the micrograph. The microsructures have a length of between about 10 μm to about 100 μm, and a width of between about 10 μm to about 100 μm.

Different microstructure morphologies are apparent for the different particles. The particles of FIGS. 6A and 6B mainly include a smooth globular microstructure, the particles of FIG. 6D mainly includes generally smooth filamentous microstructure, while the particles of FIG. 6C mainly include a rough, irregular, block-shaped microstructure.

The pore structure of the particles was also studied. Cross sections of the particles of chromogenic absorbent material were observed by scanning electron microscopy, as can be seen in FIG. 7C, and as detailed in Example 6. The cross sections were obtained by freeze-fracture under liquid nitrogen and observed by SEM to determine the pore density and equivalent diameter of the pores. It is understood that "pore density" refers to the proportion of the surface which is not covered by solid material (i.e., the ratio of the pore surface to the total surface). It is also understood that "equivalent diameter" refers to the approximate diameter of a comparable circular cylinder having the same volume as that of the pore.

Depending of the absorptive material, the particles of chromogenic absorbent material may have a pore density greater than about 20%, or greater than about 25%, or of about 27% to about 33%, for example. The pores of the particles of chromogenic absorbent material have an equivalent diameter greater than about 20 µm, or of about 20 µm to about 40 µm, or of about 20 µm to about 30 µm.

Figure 7B:
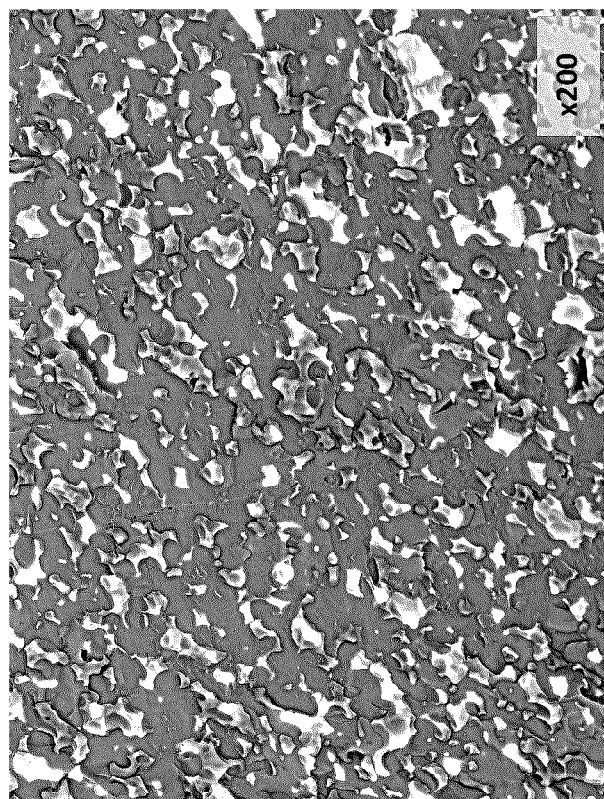
FIG. 7B is a ×200 scanning electron micrograph showing a cross section of an extruded starch particle in which gas was injected during extrusion. The cross section is obtained by freeze-fracture (comparative figure).
Figure 7A:
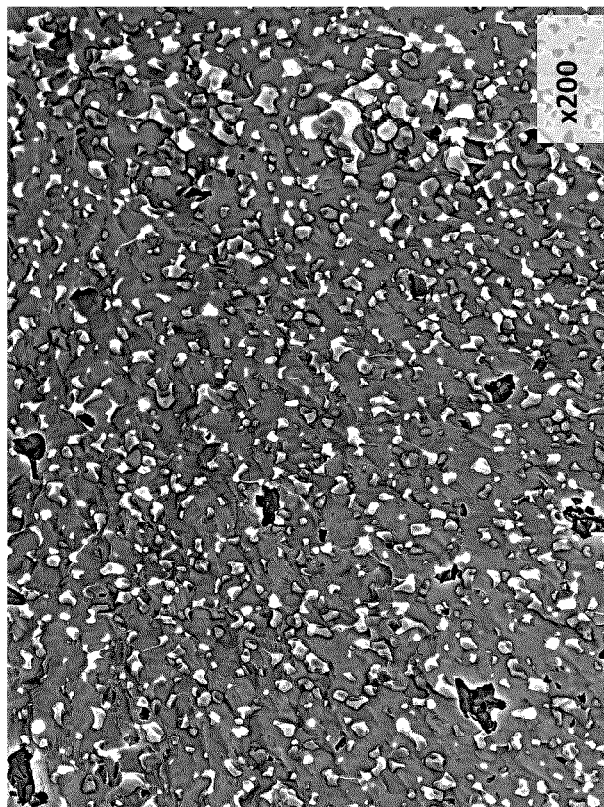
FIG. 7A is a ×200 scanning electron micrograph showing a cross section of an extruded starch particle, obtained by freeze-fracture (comparative Figure).
Figure 7C:
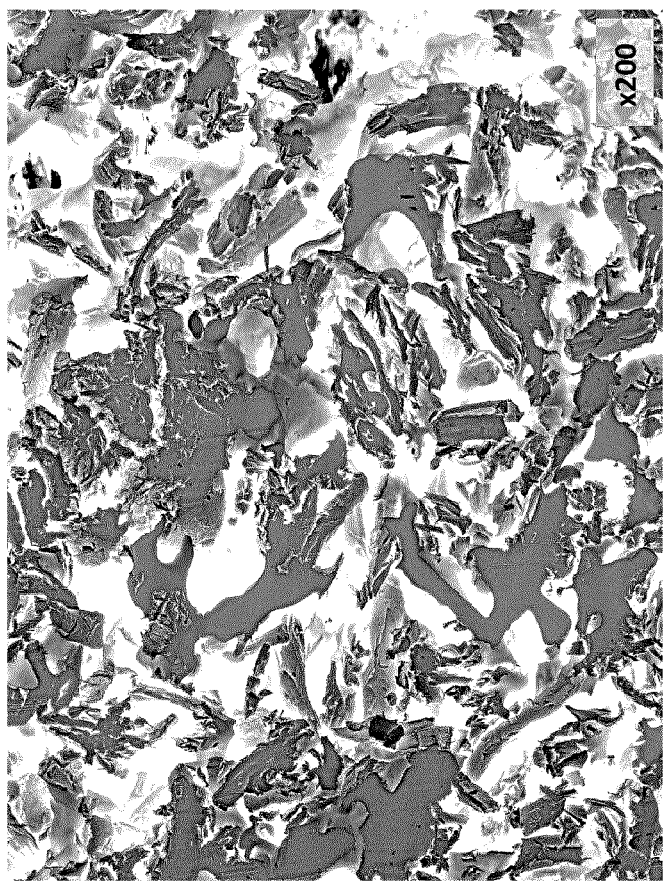
FIG. 7C is a ×200 scanning electron micrograph showing a cross section of a particle of chromogenic absorbent material in which the absorptive material includes 50% PGS and 50% MCC.
Figure 8B:
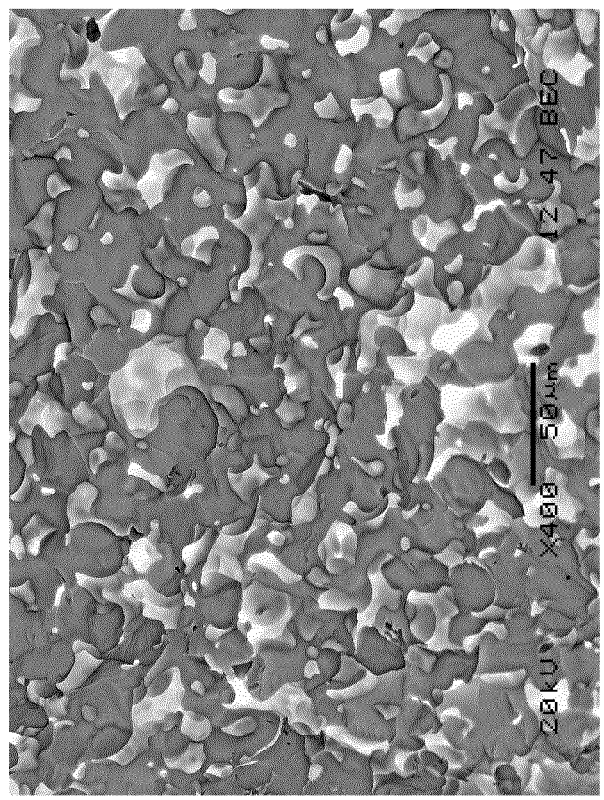
FIG. 8B is a ×400 scanning electron micrograph showing a cross section of an extruded starch particle in which gas was injected during extrusion. The cross section is obtained by freeze-fracture (comparative figure).
Figure 8A:
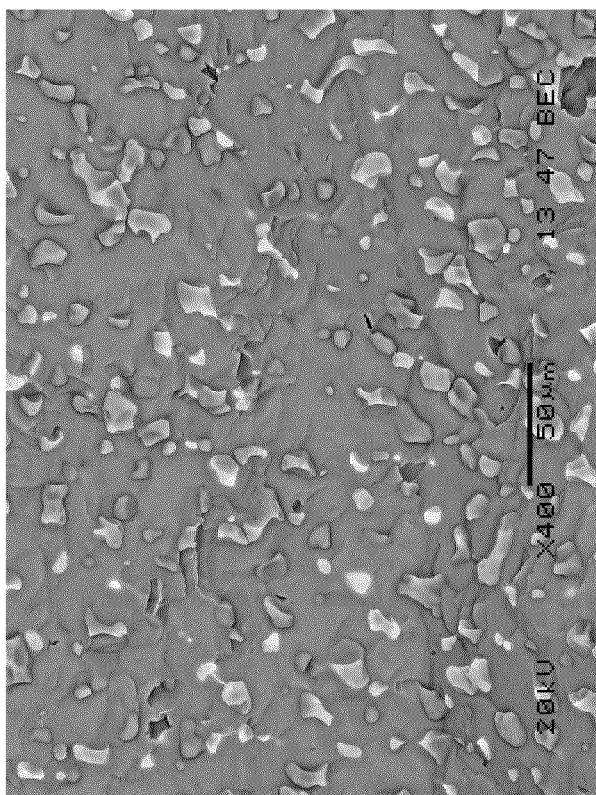
FIG. 8A is a ×400 scanning electron micrograph showing a cross section of an extruded starch particle, obtained by freeze-fracture (comparative Figure).
Figure 8C:
FIG. 8C is a ×400 scanning electron micrograph showing a cross section of a particle of chromogenic absorbent material in which the absorptive material includes 50% PGS and 50% MCC.

Cross sections of extruded starch particles were also examined as a comparative example (see also Example 6), and can be seen in FIGS. 7A and 7B.

Now referring to FIG. 1, an example of chromogenic absorbent material for detecting blood in animal excretions is described. The substance to be detected (blood) includes haemoglobin which is a pseudoperoxidase. In the absence of blood (i.e., in the absence of peroxidase and/or pseudoperoxidase), the reduction of cumene hydroperoxide (the oxidizing agent) into reduction products and the oxidation of TMB into oxidized TMB (oxTMB) is not catalyzed. When traces of blood are present (i.e., when traces of haemoglobin are present), the reactions are enabled and TMB is oxidized into oxTMB which has a distinctive blue color. The chromogenic absorbent material may be obtained to include a porous polysaccharide matrix having a low density. Thus, the chromogenic absorbent material described is suited for the detection of blood in animal excretions, and therefore for detection of urinary tract diseases for example.

Figure 2:
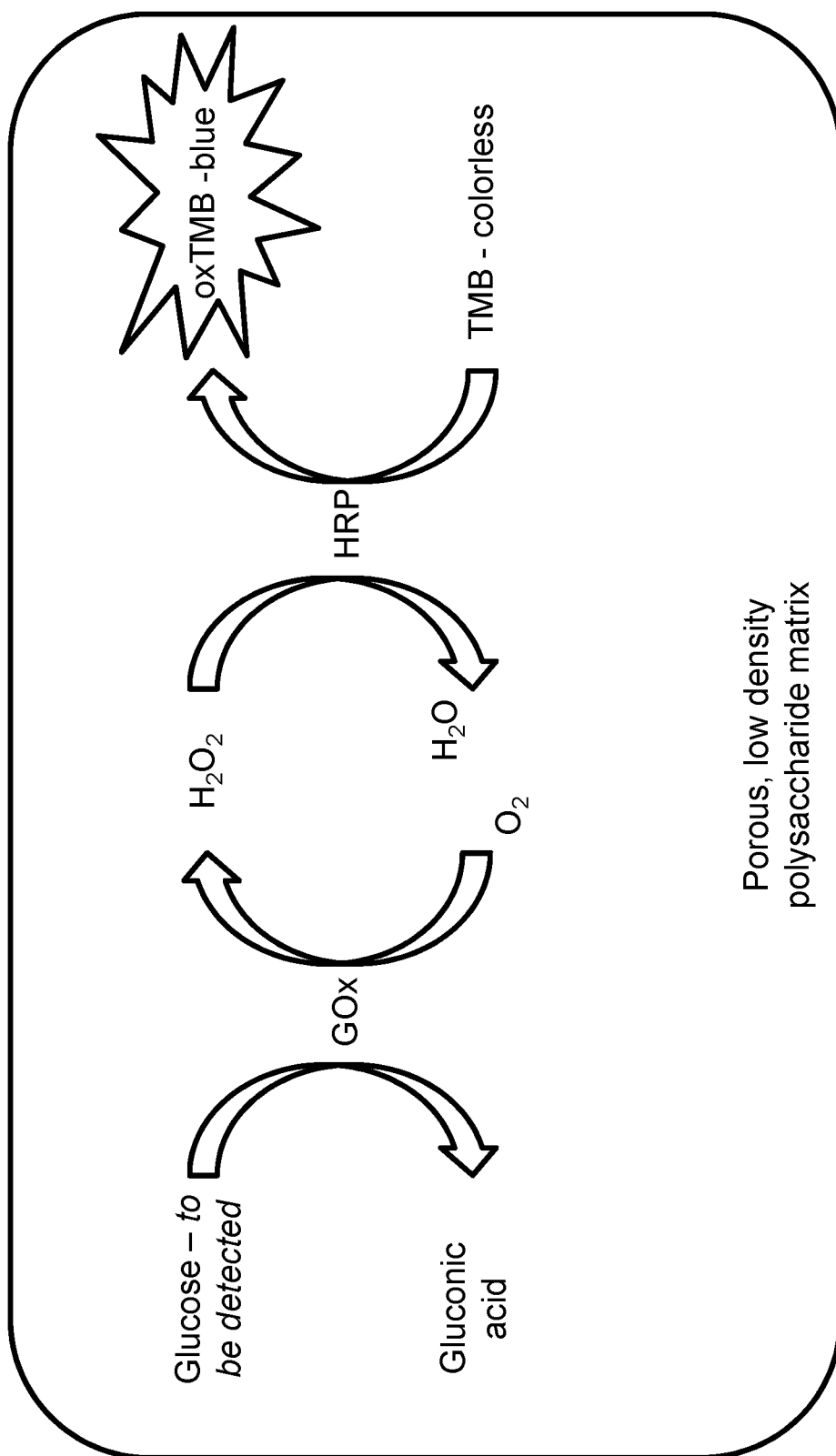
FIG. 2 is a scheme of the reaction pathway taking place in the particles of chromogenic absorbent material for the detection of glucose in animal excretions.

Now referring to FIG. 2, an example of the chromogenic absorbent material for detecting glucose in animal excretions is described. The chromogenic absorbent material used for detecting glucose includes a first catalytic compound (such as glucose oxidase) to generate hydrogen peroxide in situ. In the case of glucose detection, the chromogenic absorbent material further includes a second catalytic compound for catalyzing the oxidation of TMB and the reduction of the hydroperoxide. The second catalytic compound may be horseradish peroxidase. It is understood that other peroxidases or pseudoperoxidases may be used in other implementations. It should also be understood that in the case of glucose detection, the polysaccharide matrix does not include polysaccharides which may react with the first catalytic compound. If such polysaccharides were used, hydrogen peroxide would be generated in situ even without the presence of glucose in the animal excretions, which would lead to false positive test results. For example, when the first catalytic compound is glucose oxidase, the absorptive material does not include starches or modified starches that could react and give false positives.

Still referring to FIG. 2, when glucose is not present in the animal excretions, TMB is not oxidized, as no hydrogen peroxide is generated in situ. When glucose is present in the animal excretions, glucose oxidase oxidizes the glucose into gluconic acid and reduces oxygen into hydrogen peroxide. The horseradish peroxidase then reduces the hydrogen peroxide into water and oxidizes TMB into oxTMB which has a distinctive blue color. The chromogenic absorbent material described in FIG. 2 may be obtained to include a porous polysaccharide matrix having a low density, and is suited for detection of glucose in animal excretions, and therefore for detection of diabetes in animals for example.

In some implementations, the absorptive powder mixture used for making chromogenic particles for detecting glucose can include an oxidizing agent which is not responsive to peroxidatic/pseudoperoxidatic activity in the excretion. Such oxidizing agent can include potassium iodate, potassium bromate, or mixtures thereof. In some implementations, 0.1 wt % to 1 wt % oxidizing agent can be present in the absorptive powder mixture (for example 0.5 wt % oxidizing agent). In some implementations, the particles of chromogenic absorbent material include: a chromogenic indicator which is a pH indicator for colorimetric determination of the pH; and an absorptive material for absorbing the excretion, the absorptive material including a water-absorbing polysaccharide providing absorptive properties to the chromogenic absorbent material. The pH indicator can include any known colorimetric pH indicator, such as (and without being limitative) methyl violet, thymol blue, benzyl orange, bromophenol blue, congo red, methyl orange, methyl red, bromocresol purple, bromothymol blue, phenol red, cresol red, thymol blue, phenolphthalein, tymolphthalein, alizarin yellow R or combinations thereof. For example, the pH indicator can include a universal pH indicator such as Bogen universal indicator solution which includes bromothymol blue (as a sodium salt), phenolphthalein and methyl red.

In some implementations, the chromogenic indicator may be homogeneously dispersed throughout the absorptive material according to the preparation method of the chromogenic absorbent material. The chromogenic indicator may be present not only at the exterior surface of a given particle, but also in a neighboring sub-surface region that can be rapidly exposed to excretions that are absorbed into the particle. Additionally, when the absorptive material is glassy or substantially transparent, the presence of the chromogenic indicator in a sub-surface region allows it to be readily visible when a color change occurs and also avoids exposure to the air. In addition, the absorptive material may be provided with certain absorptive properties relative to the environment when in operation. For instance, the absorptive material may be provided to enable faster absorption of excretions compared to the surrounding material, such as surrounding animal litter, to facilitate adequate exposure of the excretions to the active agents in the chromogenic absorptive material. As different animal litters may have different absorptive properties, the absorptive material may be provided in accordance with pre-determined litter absorption properties, e.g. according to a maximum litter absorption rate. For instance, in some implementations, the absorptive material has a higher absorption rate compared to the litter material, and optionally a substantially higher absorption rate. For example, the absorptive material may have an absorption rate about 3 to 10 times higher, or about 5 to 10 times higher than the absorption rate of the litter material.

In some implementations, the process described herein can be used for manufacturing the chromogenic absorbent material.

In some implementations, the process includes:
  providing an absorptive powder including a water-absorbing polysaccharide onto a surface, thereby obtaining a powder bed;

preparing a chromogenic solution by addition of a chromogenic agent, into a solvent;
releasing the chromogenic solution from a solution dispenser so as to contact the powder bed, thereby forming a solution-impregnated humid material;
maintaining the solution-impregnated humid material supported by the surface and in substantially shear-less conditions until the solution-impregnated humid material agglomerates to produce an agglomerated humid material; and
drying the agglomerated humid material, thereby forming the chromogenic absorbent material.

In some implementations, the process includes:
providing an absorptive powder including a water-absorbing polysaccharide onto a surface, thereby obtaining a powder bed;
providing a chromogenic solution including a solvent and a chromogenic agent;
releasing the chromogenic solution from a solution dispenser so as to contact the powder bed, thereby forming a solution-impregnated humid material;
maintaining the solution-impregnated humid material supported by the surface and in substantially shear-less conditions until the solution-impregnated humid material agglomerates to produce an agglomerated humid material; and
drying the agglomerated humid material, thereby forming the chromogenic absorbent material.

In some implementations, the process includes:
providing an absorptive powder including a water-absorbing polysaccharide onto a surface, thereby obtaining a powder bed;
preparing a chromogenic solution by addition of a chromogenic agent and an oxidizing agent or by addition of the chromogenic agent and a first catalytic compound, into a solvent;
releasing the chromogenic solution from a solution dispenser so as to contact the powder bed, thereby forming a solution-impregnated humid material;
maintaining the solution-impregnated humid material supported by the surface and in substantially shear-less conditions until the solution-impregnated humid material agglomerates to produce an agglomerated humid material; and
drying the agglomerated humid material, thereby forming the chromogenic absorbent material.

In some implementations, the process includes:
providing an absorptive powder including a water-absorbing polysaccharide onto a surface, thereby obtaining a powder bed;
providing a chromogenic solution including:
  a solvent; and
  a chromogenic agent and an oxidizing agent, or a chromogenic agent and a first catalytic compound;
releasing the chromogenic solution from a solution dispenser so as to contact the powder bed, thereby forming a solution-impregnated humid material;
maintaining the solution-impregnated humid material supported by the surface and in substantially shear-less conditions until the solution-impregnated humid material agglomerates to produce an agglomerated humid material; and
drying the agglomerated humid material, thereby forming the chromogenic absorbent material.

In some implementations, the aqueous solution is released in the form of discrete drops onto the powder bed such that the agglomerated humid material is produced in the form of agglomerated humid particles and the chromogenic absorbent material is produced in the form of particles of chromogenic absorbent material.

In some implementations wherein the absorptive powder includes at least a second polysaccharide, the process can further include mixing together the water-absorbing polysaccharide, the second polysaccharide and any further optional component such as a superabsorbent polymer.

The chromogenic solution includes the chromogenic agent and can further include the oxidizing agent or a first catalytic compound for generating the oxidizing agent in situ. In the case of chromogenic solutions used for making particles of chromogenic absorbent material for the detection of glucose in an excretion, the chromogenic solution further includes a second catalytic compound. For example, the second catalytic compound includes a peroxidase, a pseudoperoxidase, or a mixture thereof. In the case of a chromogenic solution used for measuring the pH of an excretion, the chromogenic solution includes a pH indicator (or a combination of pH indicators).

Optionally, the chromogenic solution may include a buffering agent so as to maintain a pH of the chromogenic solution between 5 and 7. Extreme pH may be avoided.

Optionally, the chromogenic solution may include a colour enhancer, a stabilizer, a metal-scavenger agent or a combination thereof as defined herein.

In an optional aspect, the chromogenic solution may be prepared and tailored to the particular absorptive material.

In some implementations, releasing the chromogenic solution includes pouring the chromogenic solution under gravity onto the powder bed. In some implementations, pouring the chromogenic solution includes dripping the aqueous solution in the form of discrete drops onto the powder bed such that the agglomerated humid material is produced in the form of discrete humid particles.

It is understood that the implementations of the process described in the section "Process for manufacturing particles of water-absorbing material" can be applied to the manufacturing of the particles of chromogenic absorbent material.

Chromogenic Absorbent Material for Use in the Detection of Chemical and/or Biological Species In some embodiments, there is provided a chromogenic water-absorbing material for detecting certain compounds (which may be indicative of diseases) in a water-containing medium (i.e., excretions, blood, plasma, saliva, an aqueous solution or a solid which is impregnated with an aqueous solution, or a moistened gas). The process described herein can be used for manufacturing such chromogenic water-absorbing material.

In some implementations, a chromogenic absorbent material is provided for detecting a detectable substance in a water-containing medium. In some implementations, the chromogenic absorbent material includes:
  a trigger agent;
  a chromogenic indicator convertible into a chromogenically active substance in the presence of the trigger agent and the detectable substance; and
  an absorptive material for absorbing the animal excretion, the absorptive material being porous and including:
    a water-absorbing polysaccharide providing absorptive properties to the chromogenic absorbent material; and
    a second polysaccharide providing structural integrity to the chromogenic absorbent material.

In some implementations, the trigger agent is responsive to the presence of the detectable substance. In some implementations, the trigger agent enables a reaction between the detectable substance and the chromogenic indicator—in such case, it is understood that the trigger agent may not necessarily be directly responsive to the presence of the detectable substance.

In some implementations, the chromogenic absorbent material includes:
- a trigger agent;
- a chromogenic indicator convertible into a chromogenically active substance in the presence of the trigger agent and the detectable substance; and
- an absorptive material which is porous, for absorbing the water-containing medium, the absorptive material including:
  - a water-absorbing polysaccharide providing absorptive properties to the chromogenic absorbent material; and
  - a second polysaccharide providing structural integrity to the chromogenic absorbent material, the trigger agent, the chromogenic indicator and the detectable substance being unreactive to the absorptive material.

In some implementations, the chromogenic absorbent material includes:
- a trigger agent;
- a chromogenic indicator convertible into a chromogenically active substance in the presence of the trigger agent and the detectable substance; and
- an absorptive material which is porous, for absorbing the water-containing medium, the absorptive material comprising a water-absorbing polysaccharide providing absorptive properties to the chromogenic absorbent material,
- wherein the chromogenic absorbent material has a density of about 0.20 g/cm$^3$ to about 0.39 g/cm$^3$,
- the trigger agent, the chromogenic indicator and the detectable substance being unreactive to the absorptive material.

In some implementations, the chromogenic absorbent material includes:
- a trigger agent;
- a chromogenic indicator convertible into a chromogenically active substance in the presence of the trigger agent and the detectable substance; and
- an absorptive material which is porous, for absorbing the water-containing medium, the absorptive material comprising a water-absorbing polysaccharide providing absorptive properties to the chromogenic absorbent material,
- wherein the chromogenic absorbent material is a porous material having an effective porosity of about 0.5 mL/g to about 2.0 mL/g,
- the trigger agent, the chromogenic indicator and the detectable substance being unreactive to the absorptive material.

It is understood that the trigger agent may be selected depending on the detectable substance and such that the conversion of the chromogenic indicator into a chromogenically active substance takes place and/or is catalyzed only if both the trigger agent and the detectable substance are present. For example, when the detectable substance is a peroxidase or a pseudoperoxidase, the trigger agent may be an oxidizing agent responsive to peroxidatic/pseudoperoxidatic activity in the water-containing substance and the conversion of the chromogenic indicator includes oxidation into the chromogenically active substance. As another example, the detectable substance can be reactive to the chromogenic indicator in the presence of the trigger agent, or the reaction between the chromogenic indicator and the detectable substance can be catalyzed by the trigger agent.

In some implementations, the detectable substance includes a pseudoperoxidase (such as blood which includes haemoglobin), and the trigger agent is a hydroperoxide (such as cumene hydroperoxide) or a hydroperoxide precursor.

In some implementations, the detectable substance is glucose, and the trigger agent is a catalytic system including an oxido-reductase and a peroxidase, or an oxido-reductase and a pseudoperoxidase. For example, the oxido-reductase may be glucose oxidase and the peroxidase may be horseradish peroxidase.

Preferably, the detectable substance, the trigger agent and the chromogenic absorbent are unreactive to the absorptive material. In other words, the components of the absorptive material may be selected such that they do not react with the trigger agent, the detectable substance and the chromogenic indicator. For example, when the detectable substance is glucose and the trigger agent is a catalytic system including an oxido-reductase and a peroxidase, or an oxido-reductase and a pseudoperoxidase, the components of the absorptive material are selected so that they do not include starch or any other polysaccharide which can react similarly to glucose.

In some embodiments, the chromogenic absorbent material can be used in the detection of other types of diseases or conditions, by using appropriate trigger agent and chromogenic indicator. For example, similar compounds which are used in urine test strips may be used as trigger agents and chromogenic indicator in conjunction with the absorptive material in order to detect certain chemicals indicative of diseases or conditions. For example, the chemicals to be detected (i.e., the detectable substance) may be haemoglobin or glucose as discussed above, or proteins, ketone bodies, bilirubin, urobilinogen, nitrites or leukocytes (via detection of leukocyte esterase). It is understood that other detectable substance or diseases can be detected by using the appropriate trigger agent, chromogenic absorbent, and absorptive material. Examples of various detection systems which may be used with the absorptive material described herein are shown in Table A below.

TABLE A

| Examples of chromogenic systems usable with the water-absorbing material | | | |
|---|---|---|---|
| To be detected | Detectable substance | Trigger agent | Chromogenic indicator |
| Presence of blood | Haemoglobin or myoglobin | oxidizing agent responsive to the pseudoperoxidatic activity of Haemoglobin (e.g. a peroxide) | responsive to the oxidizing activity of the oxidizing agent (e.g. a benzidine) |

TABLE A-continued

Examples of chromogenic systems usable with the water-absorbing material

| To be detected | Detectable substance | Trigger agent | Chromogenic indicator |
|---|---|---|---|
| Diabetes, glycosuria | Glucose | A catalytic system for in situ generation of an oxidizing agent and for oxidizing the chromogenic indicator (e.g. oxido-reductase and peroxidase) | responsive to the oxidizing activity of the oxidizing agent (e.g. a benzidine) |
| Proteinuria | Proteins in urine (e.g. albumine) | Acidic buffer for protonating the amino groups of the proteins | pH indicator responsive to the protonated amino groups of the proteins (e.g. tetrabromophenol blue, 3',3'',5',5''-tetrachlorophenol, or 3,4,5,6-tetrabromosulfonphthalein) |
| Ketonuria | Ketone bodies (e.g. acetoacetate, beta-hydroxybutyric acid, acetone) | Alkali buffer for enabling the reaction between the ketone bodies and the chromogenic indicator (e.g. NaOH) | Metal complex reactive to ketone bodies (e.g. Sodium nitroprusside) |
| Liver disease-bilirubin testing | Bilirubin glucuronide | Acidic buffer for enabling the reaction between bilirubin glucuronide and chromogenic indicator | Diazonium salt reactive with bilirubin glucuronide (e.g. 2,6-dichlorobenzene-diazonium-tetrafluoroborate) |
| Urinary infection by gram-negative bacteria - nitrite testing | Nitrite anion ($NO_2^-$) | Acidic buffer for enabling the reaction between nitrite and chromogenic indicator | A chromogenic system including: (i) an aromatic amine (e.g. p-arsanilic acid) reactive with nitrite ions to form a diazonium salt; and (ii) a quinoline compound reactive with the diazonium salt to form a chromogenically active substance (e.g. tetrahydrobenzoquinoline) |
| Urinary infection - leukocyte testing | Leukocyte esterase | Compound which is decomposable via catalytic reaction of leukocyte esterase (e.g. indolecarboxylic acid ester) to form a product able to react with the chromogenic indicator (e.g. indoxyl) | Diazonium salt reactive with the decomposition product (e.g. 2,6-dichlorobenzene-diazonium-tetrafluoroborate) to yield a chromogenically active substance |
| Urine specific gravity | Cations present in solution | Polyelectrolyte (e.g. poly (methyl vinyl ether/maleic anhydride or Ethylene Glycol-bis(aminoethyl ether) tetraacetate - EGTA) in alkaline buffer | pH indicator (e.g. Bromothymol blue) |

In some implementations, the chromogenic absorbent material can be adapted for use in the detection of biological species, such as for the detection of specific proteins (e.g., proteins produced by cancer cells), bacteria (e.g., *E. Coli*, tuberculosis), viruses (e.g., flu virus, HIV, hepatitis), yeast or fungi (e.g., *candida, aspergillus* or *cryptococcus*).

In some implementations, the chromogenic absorbent material can be adapted for the detection of ovulation in an animal or in a human. As certain hormones are specifically produced during ovulation, such hormones may be found in urine. Using specific markers for the detection of such hormones in the absorptive material can allow for the detection of ovulation.

In some implementations, the chromogenic absorbent material may be used for detecting pollutants in water such as in the drinking water system or in a swimming pool. The pollutants can include bacteria, metals, pesticides, certain toxic ions such as nitrates.

In some implementations, the chromogenic absorbent material may be used for the detection of impurities in a gas, such as carbon monoxide in air. In some scenarios, the gas to be tested can be bubbled through an aqueous solution in order to solubilize some of the constituents of the gas into the solution, and the aqueous solution can then be contacted with a chromogenic absorbent material which includes appropriate trigger agent and chromogenic indicator.

In some implementations, the chromogenic absorbent material can be used for the detection of traces of humidity, in a gas such as air. For example, the chromogenic absorbent material can include a chromogenic indicator responsive to the presence of water (e.g., anhydrous $CuSO_4$), and can be exposed to the gas. Water molecules present in the absorbent material can be absorbed by the material, and interact with the chromogenic indicator. It is to be noted that in this scenario, no trigger agent is required in order to enable the color change.

It is understood that the absorbent material may be used in an animal litter (such as cat litter or puppy pads) for detecting the diseases and conditions mentioned herein in animals, or may be used in a hygiene product for humans (e.g., a diaper) for detecting the diseases and conditions mentioned herein in humans.

Use of the Absorbent Material for Detecting Chemical and/or Biological Species with Subsequent Addition of Chromogenic Indicator In some implementations, the chromogenic indicator may not be present in the composition of the absorbent material, and may be added after the absorbent material has made contact with the detectable substance in the water-containing medium.

For example, in the case of blood detection, the water-containing medium can first be contacted with the absorbent material. A chromogenic solution including the oxidizing agent and the chromogenic indicator can subsequently be contacted with the absorbent material. It is understood that the chromogenic solution may be added in various ways, such as by vaporizing the chromogenic solution onto the absorbent material. The chromogenic indicator can therefore be activated if blood is present in the water-containing medium. It is also understood that using a water-absorbing material which does not include a chromogenic indicator, and subsequently adding the chromogenic indicator for detecting a detectable substance can be performed with many of the diseases or compounds listed herein, as will be recognized by a person skilled in the art.

In some embodiments, there is provided a water-absorbing material for detecting certain compounds (which may be indicative of diseases) in a water-containing medium (i.e., excretions, blood, plasma, saliva, an aqueous solution or a solid which is impregnated with an aqueous solution, or a moistened gas), by contacting a chromogenic indicator with the water-absorbing material impregnated with the water-containing medium. The chromogenic indicator can be solubilized in a chromogenic solution, and the chromogenic solution can be contacted with the water-absorbing material impregnated with the water-containing medium. The process described herein can be used for manufacturing such water-absorbing material.

In some implementations, the absorbent material includes:
a trigger agent for detecting the presence of the detectable substance when a chromogenic indicator is added to the absorbent material, the chromogenic indicator being convertible into a chromogenically active substance in the presence of the trigger agent and the detectable substance; and
an absorptive material which is porous, for absorbing the water-containing medium, the absorptive material including:
a water-absorbing polysaccharide providing absorptive properties to the absorbent material; and
a second polysaccharide providing structural integrity to the absorbent material,
the trigger agent and the detectable substance being unreactive to the absorptive material.

In some implementations, the chromogenic absorbent material includes:
a trigger agent for detecting the presence of the detectable substance when a chromogenic indicator is added to the absorbent material, the chromogenic indicator being convertible into a chromogenically active substance in the presence of the trigger agent and the detectable substance; and
an absorptive material which is porous, for absorbing the water-containing medium, the absorptive material comprising a water-absorbing polysaccharide providing absorptive properties to the absorbent material,
wherein the chromogenic absorbent material has a density of about 0.20 $g/cm^3$ to about 0.39 $g/cm^3$,
the trigger agent and the detectable substance being unreactive to the absorptive material.

In some implementations, the chromogenic absorbent material includes:
a trigger agent for detecting the presence of the detectable substance when a chromogenic indicator is added to the absorbent material, the chromogenic indicator being convertible into a chromogenically active substance in the presence of the trigger agent and the detectable substance; and
an absorptive material which is porous, for absorbing the water-containing medium, the absorptive material comprising a water-absorbing polysaccharide providing absorptive properties to the absorbent material,
wherein the chromogenic absorbent material is a porous material having an effective porosity of about 0.5 mL/g to about 2.0 mL/g,
the trigger agent and the detectable substance being unreactive to the absorptive material.

Other Uses of the Water-Absorbing Material

In some implementations, a compound for a specific use can be incorporated into the water-absorbing material. In some implementations, such compounds can be incorporated directly in the powder mixture, prior to contacting the powder mixture with the aqueous solution. In other implementations, such compounds can be incorporated in the aqueous solution which is contacted with the powder mixture. For example, solid compounds can be added via the powder mixture, and water-soluble compounds or liquids can be added via the aqueous solution. It is understood that for each given compound, there may be several ways of incorporating the compound into the water-absorbing material.

In some implementations, the water-absorbing material can be used as a desiccant or as part of a desiccant mixture, for example to absorb humidity in air by exposing the desiccant to ambient air or a water-comprising gas.

In some implementations, the water-absorbing material can be adapted for detecting Ultra Violet radiation, for example by incorporating an agent which becomes chromogenically active when exposed to UV radiation. Non-limiting examples of such agent include chlorophyll or quinine sulfate, which become fluorescent when exposed to UV radiation.

In some implementations, the water-absorbing material can be adapted for detecting urine, for example by incorporating an agent which becomes chromogenically active when exposed to urine.

In some implementations, the water-absorbing material can be used as a support for a flavor enhancer or as a support for a perfume enhancer. For example, maltol can be incorporated into the water-absorbing material.

In some implementations, the water-absorbing material can be adapted for use as an anti-odor material in conjunction with an anti-odor agent. For example, N-BTPT can be incorporated into the water-absorbing material.

In some implementations, the water-absorbing material can be used as fish bait. For example, compounds which are edible by fish can be incorporated into the water-absorbing material, and the water-absorbing material can be directly used as bait. Non-limiting examples of compounds include fish flour, fish oil or compositions which include amino acids.

In some implementations, the water-absorbing material can be used as a perfume carrier, for example by incorporating a perfume in the water-absorbing material. In some implementations, the perfume can be incorporated at between 10 wt % and 100 wt %, or between 50 wt % and 100 wt %, or again at about 100 wt % of the water-absorbing material.

EXAMPLES & EXPERIMENTATION

Experimentation Series 1

Experiments were performed by preparing particles of chromogenic absorbent material (i.e. particles of water-absorbing material) having different compositions and testing the particles when contacted with a blood-containing solution.

Particles of chromogenic absorbent material were prepared by mixing pregelatinized starch (PGS), microcrystalline cellulose (MCC) and sodium polyacrylate as the superabsorbent polymer (SAP), in powder form, thereby obtaining an absorptive powder mixture; The absorptive powder mixture was disposed onto a laboratory bench top to obtain a powder bed; the chromogenic solution was dripped onto the powder bed to obtain solution-impregnated humid particles; the solution-impregnated humid particles were maintained immobile on the bench top (i.e. in substantially shear-less conditions) for several seconds until the solution-impregnated humid particles agglomerated into stable agglomerated humid particles; and agglomerated humid particles were dried in an oven at 65° C. to obtain the particles of chromogenic absorbent material. In this case, the particles of chromogenic absorbent material were obtained in the form of granules having a length of between about 0.25 cm and about 0.75 cm.

The chromogenic solution I that was used is detailed in Table 1:

TABLE 1

| Compound | Molar mass (g/mol) | Mass or volume | Concentration (mmol/L) |
|---|---|---|---|
| Water (solvent) | — | 50 mL | — |
| Acetone (solvent) | — | 50 mL | — |
| TMB (chromogenic indicator) | 240.34 | 312 mg | 13 |
| CHP (oxidizing agent) | 152.19 | 114 mg | 7.5 |
| 4-lepidine (color enhancer) | 143.19 | 107 mg | 7.5 |
| Polyvinylpyrrolidone (stabilizer) | — | 30 mg | — |
| Ascorbic acid (stabilizer) | 176.12 | 20 mg | 1.15 |

The particles of chromogenic absorbent material were prepared with varying ratios of PGS/MCC and a varying amount of sodium polyacrylate-based SAP, and are numbered as shown in Table 2:

TABLE 2

| | 0 wt. % sodium polyacrylate | 1 wt. % sodium polyacrylate | 2 wt. % sodium polyacrylate | 3 wt. % sodium polyacrylate |
|---|---|---|---|---|
| 35% PGS/65% MCC | 1 | 2 | 3 | 4 |
| 40% PGS/60% MCC | 5 | 6 | 7 | 8 |
| 45% PGS/55% MCC | 9 | 10 | 11 | 12 |
| 55% PGS/45% MCC | 13 | 14 | 15 | 16 |
| 60% PGS/40% MCC | 17 | 18 | 19 | 20 |
| 65% PGS/35% MCC | 21 | 22 | 23 | 24 |

The particles of chromogenic absorbent material shown in Table 2 were placed on a bentonite-based litter and contacted with 5 mL of a 0.0215% blood solution or 5 mL of demineralized water which did not contain blood. Particles which were not contacted with any solution were also placed on the litter as a negative control.

FIGS. 3A, 3B, 3C and 3D illustrate samples as numbered in Table 2, and placed on a bentonite-based litter. In each figure, the top picture shows the granules 30 minutes after contact with the solutions, the middle picture shows the granules 2 hours after contact, and the bottom picture shown the granules 18 hours after contact. In each picture of each Figure, the top row of granules is the negative control; the middle row shows granules contacted with 5 mL of demineralized water which did not contain blood; and the bottom row shows granules contacted with 5 mL of a 0.0215% blood solution.

Figure 3A:
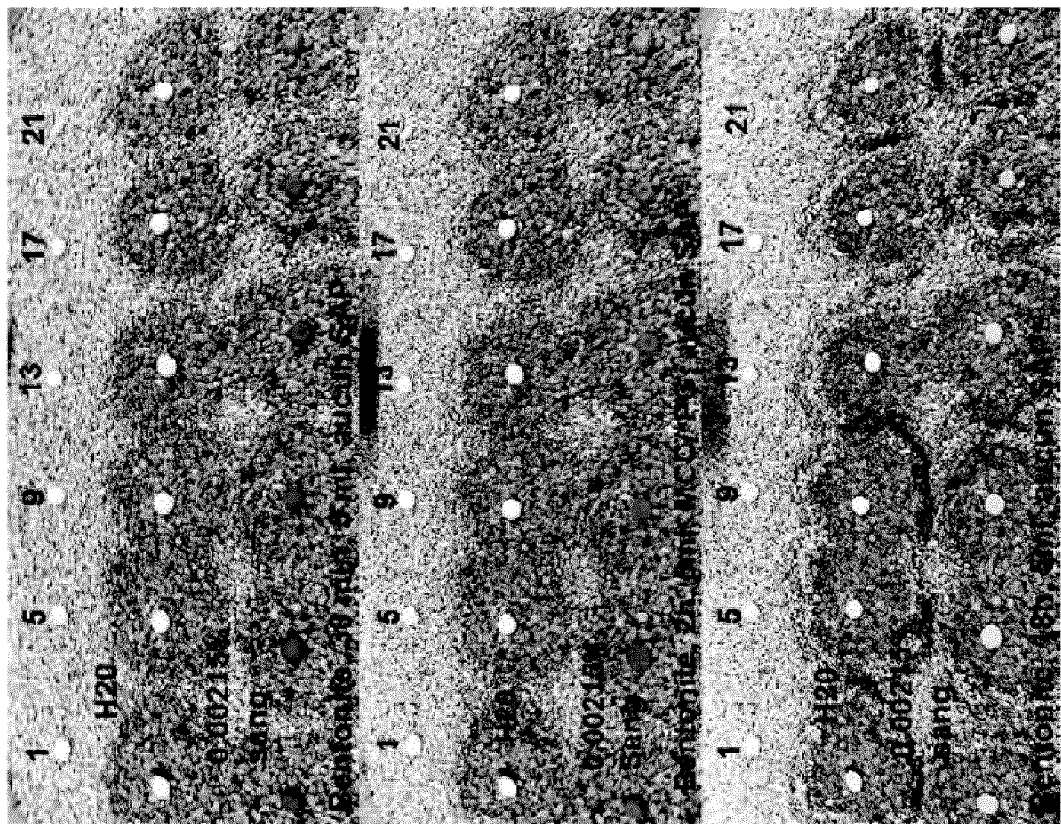
FIG. 3A shows photographs of six samples of particles of chromogenic absorbent materials after 30 minutes, 2 hours and 18 hours of contact with a diluted blood solution.

As can be seen in FIG. 3A, granules No. 1, 5, 9, 13, 17 and 21 were contacted with the different solutions (these granules contained 0 wt. % of superabsorbent polymer). The granules contacted with demineralized water did not change color and had the same white color as the negative control granules 30 mins, 2 h and 18 h after contact. The granules contacted with the blood solution had already turned blue 30 mins after contact. The blue coloration was distinctive. 2 h after contact, the blue coloration was still distinctive and present. 18 h after contact, the blue coloration had faded and the granules turned off-white or yellow. The blue coloration was present and distinctive for about 8 hours before fading.

Figure 3B:
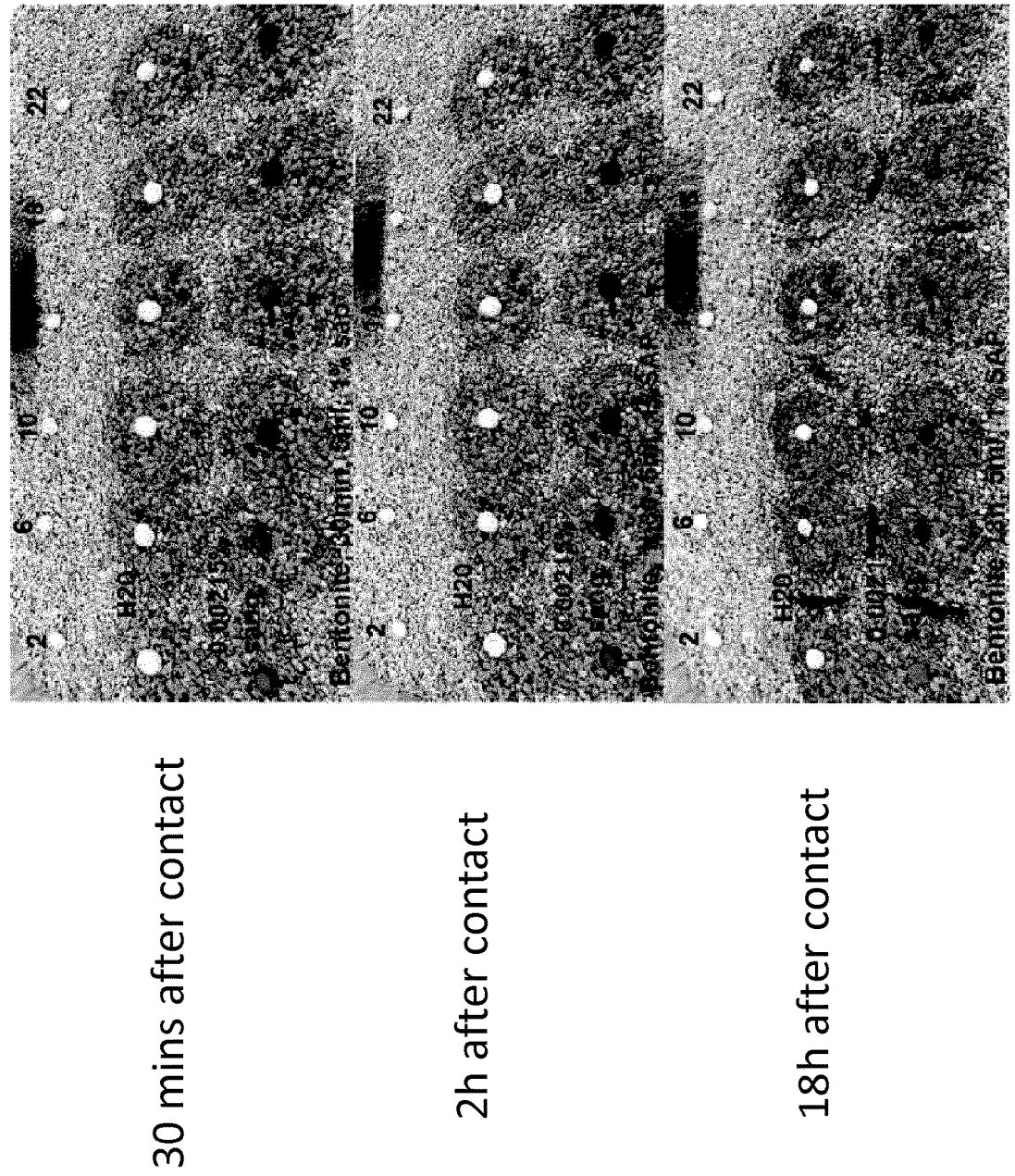
FIG. 3B shows photographs of six samples of particles of chromogenic absorbent materials including 1% of superabsorbent polymer after 30 minutes, 2 hours and 18 hours of contact with a diluted blood solution.

As can be seen in FIG. 3B, granules No. 2, 6, 10, 14, 18 and 22 were contacted with the different solutions (these granules contained about 1 wt. % of superabsorbent polymer). The granules contacted with demineralized water did not change color and had the same white color as the negative control granules 30 mins, 2 h and 18 h after contact. The granules contacted with the blood solution had already turned blue 30 mins after contact. The blue coloration was distinctive. 2 h after contact, the blue coloration was still distinctive and present. 18 h after contact, the blue coloration was still distinctive and present. The addition of 1 wt. % SAP had a positive effect on the retention of blue coloration in the granules after contact with a blood solution.

Figure 3C:
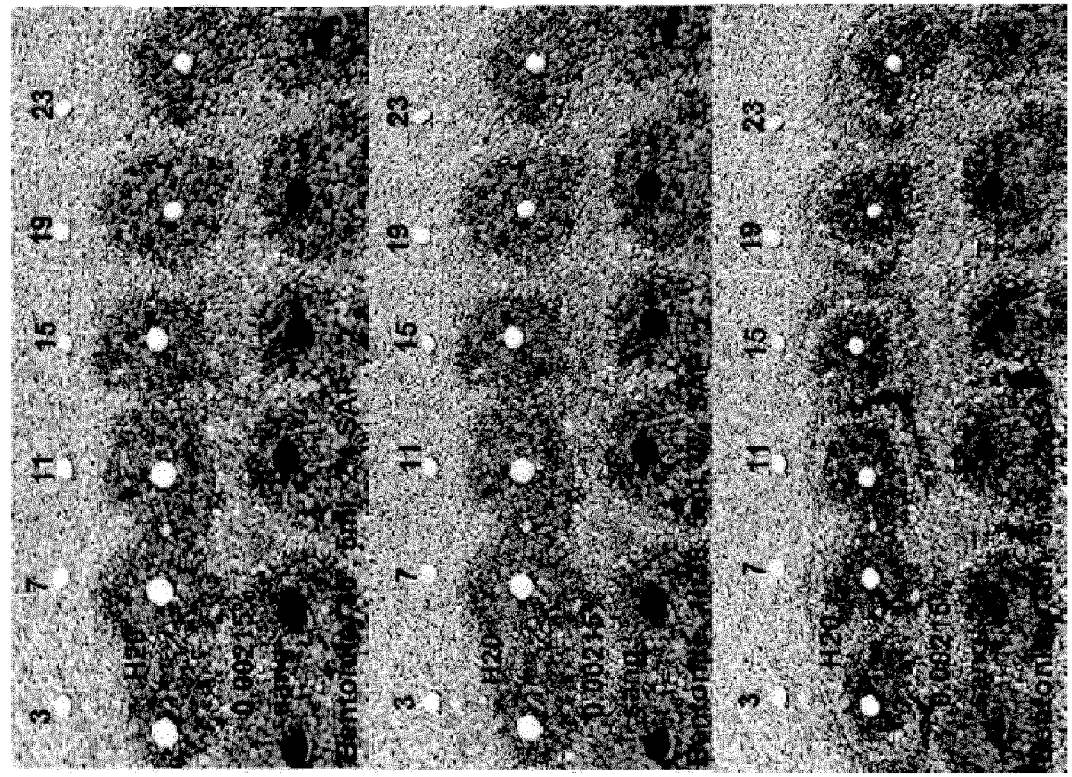
FIG. 3C shows photographs of six samples of particles of chromogenic absorbent materials including 2% of superabsorbent polymer after 30 minutes, 2 hours and 18 hours of contact with a diluted blood solution.

As can be seen in FIG. 3C, granules No. 3, 7, 11, 15, 19 and 24 were contacted with the different solutions (these granules contained about 2 wt. % of superabsorbent polymer). The same results as the ones observed and illustrated in FIG. 3B were obtained.

Figure 3D:
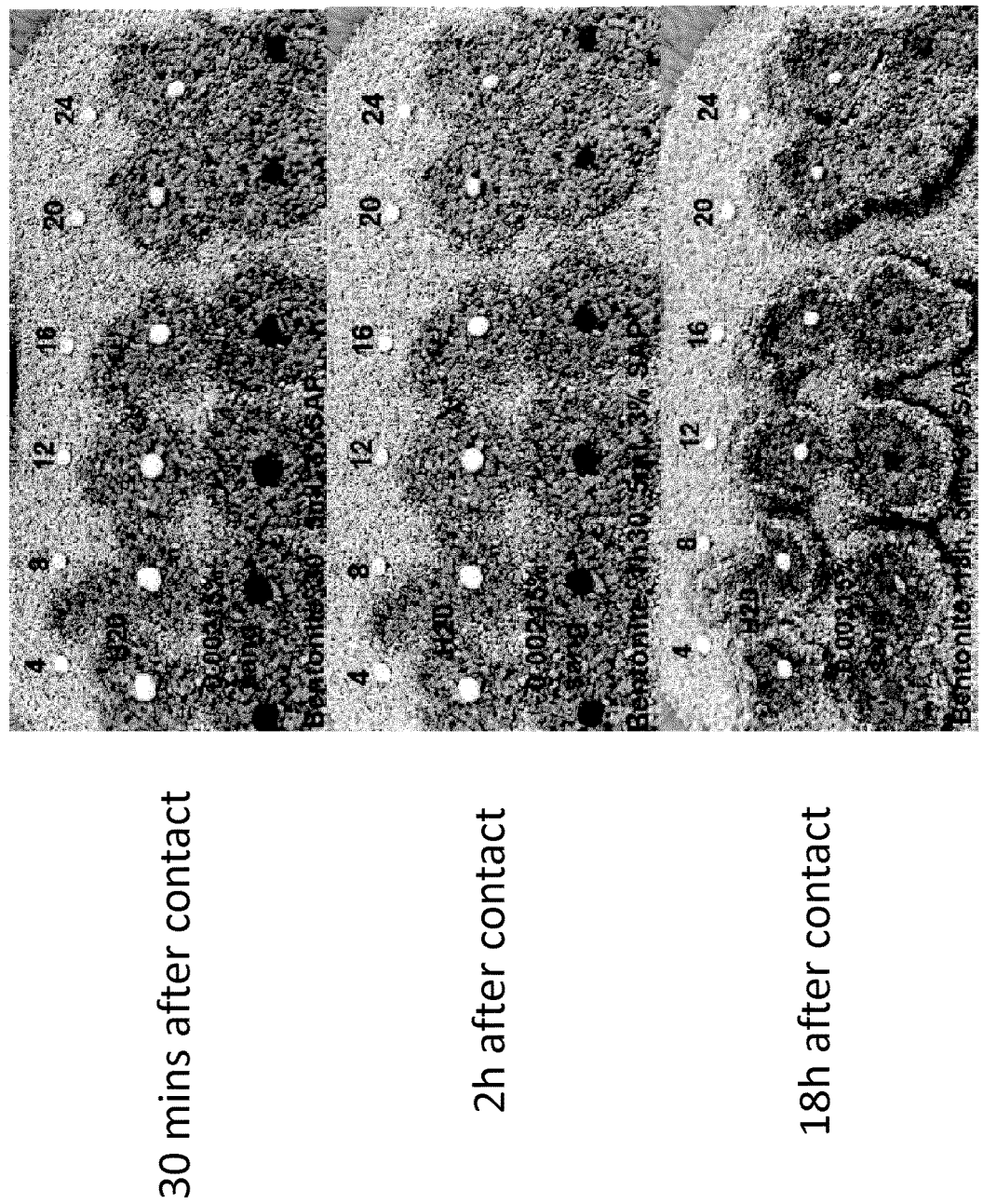
FIG. 3D shows photographs of six samples of particles of chromogenic absorbent materials including 3% of superabsorbent polymer after 30 minutes, 2 hours and 18 hours of contact with a diluted blood solution.

As can be seen in FIG. 3D, granules No. 4, 8, 12, 16, 20 and 25 were contacted with the different solutions (these granules contained about 3 wt. % of superabsorbent polymer). The same results as the ones observed and illustrated in FIGS. 3B and 3C were obtained.

Experimentations Series 2

Experiments were performed by preparing particles of chromogenic absorbent material using different polysaccharides and mixtures thereof, and testing said particles when contacted with a blood-containing solution. The polysaccharides used in this Example were pregelatinized starch (PGS), microcrystalline cellulose (MCC) and carboxymethylcellulose (CMC).

The particles were prepared as described in Example 1. No superabsorbent polymer was used in this Example and the mixing step was not performed when only one polysaccharide was used. The same chromogenic solution I as described in Example 1 was also used.

Particles of chromogenic absorbent material were prepared using various polysaccharides and mixtures thereof, and are numbered as shown in Table 3.

TABLE 3

| Polysaccharide or polysaccharide mixture | Sample number |
| --- | --- |
| 50% PGS/50% MCC | 25 |
| 100% CMC | 26 |
| 100% PGS | 27 |

Figure 4:
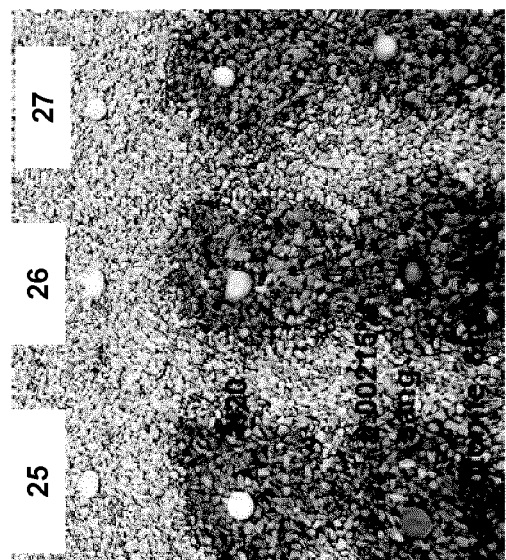
FIG. 4 shows photographs of three samples of particles of chromogenic absorbent materials including after 6 h30 and 22 hours of contact with a diluted blood solution.
Figure 4:
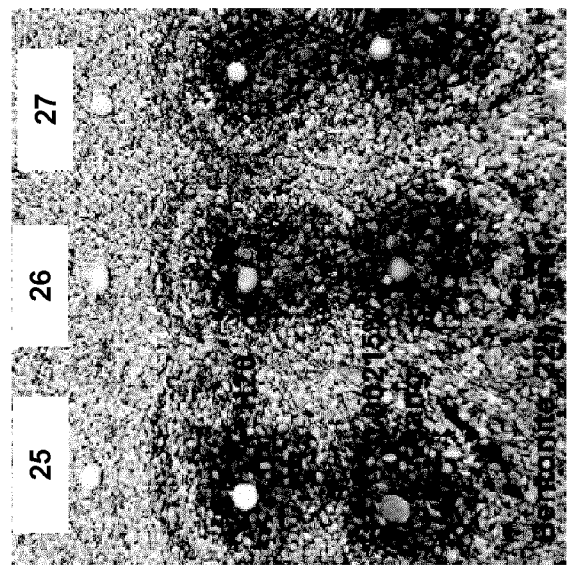

FIG. 4 shows the granules 6 h30 and 22 h after contact with 5 mL of demineralized water which did not contain blood (middle row) or 5 mL of a 0.0215% blood solution (bottom row). The top row is the negative control showing granules which were not contacted with either solution. A deep blue coloration rapidly appeared a few minutes after contact with the blood-containing solution (not shown). The granules contacted with demineralized water stayed substantially white or became slightly yellow. After 6 h30, samples No. 25 and 26 retained the deep blue coloration, while the blue coloration of sample No. 27 was lighter. After 22 h, sample No. 25 retained the deep blue coloration, sample No. 26 had a light blue coloration, and the coloration of sample No. 27 had substantially faded.

It is to be noted that all the samples prepared enable the detection of blood. Using 50% PGS/50% MCC as the absorptive material enabled the blue coloration to be retained for a longer period when compared with 100% CMC and 100% PGS granules.

Experimentation Series 3

Experiments have been performed by preparing particles of chromogenic absorbent material using a mixture of 50% microcrystalline cellulose (MCC) and 50% carboxymethyl cellulose (CMC) as the absorptive material, and different chromogenic solutions. Said particles were contacted with glucose-containing solutions.

The composition of the chromogenic solution II is detailed in Table 4.

TABLE 4

| Solvents and compounds | Mass or volume |
| --- | --- |
| Water (solvent) | 50 mL |
| Acetone (solvent) | 50 mL |
| TMB (chromogenic indicator) | 312 mg |
| Glucose oxidase (first catalytic compound) | 6 mg |
| Horseradish peroxidase (second catalytic compound) | 5 mg |

Chromogenic solution II shown in Table 4 was diluted at ratios of 1:2 and 1:10 to obtain chromogenic solutions III (1:2 dilution) and IV (1:10 dilution).

Particles of chromogenic absorbent material were prepared by mixing carboxymethyl cellulose (CMC) and microcrystalline cellulose (MCC), thereby obtaining an absorptive powder mixture; The absorptive powder mixture was disposed onto a laboratory bench top to obtain powder beds; chromogenic solutions II, III or IV were dripped onto the powder beds to obtain solution-impregnated humid particles; the solution-impregnated humid particles were maintained immobile on the bench top (i.e. in substantially shear-less conditions) for several seconds until the solution-impregnated humid particles agglomerated into stable agglomerated humid particles; and the agglomerated humid particles were dried in an oven at 65° C. to obtain the particles of chromogenic absorbent material.

Figure 5:
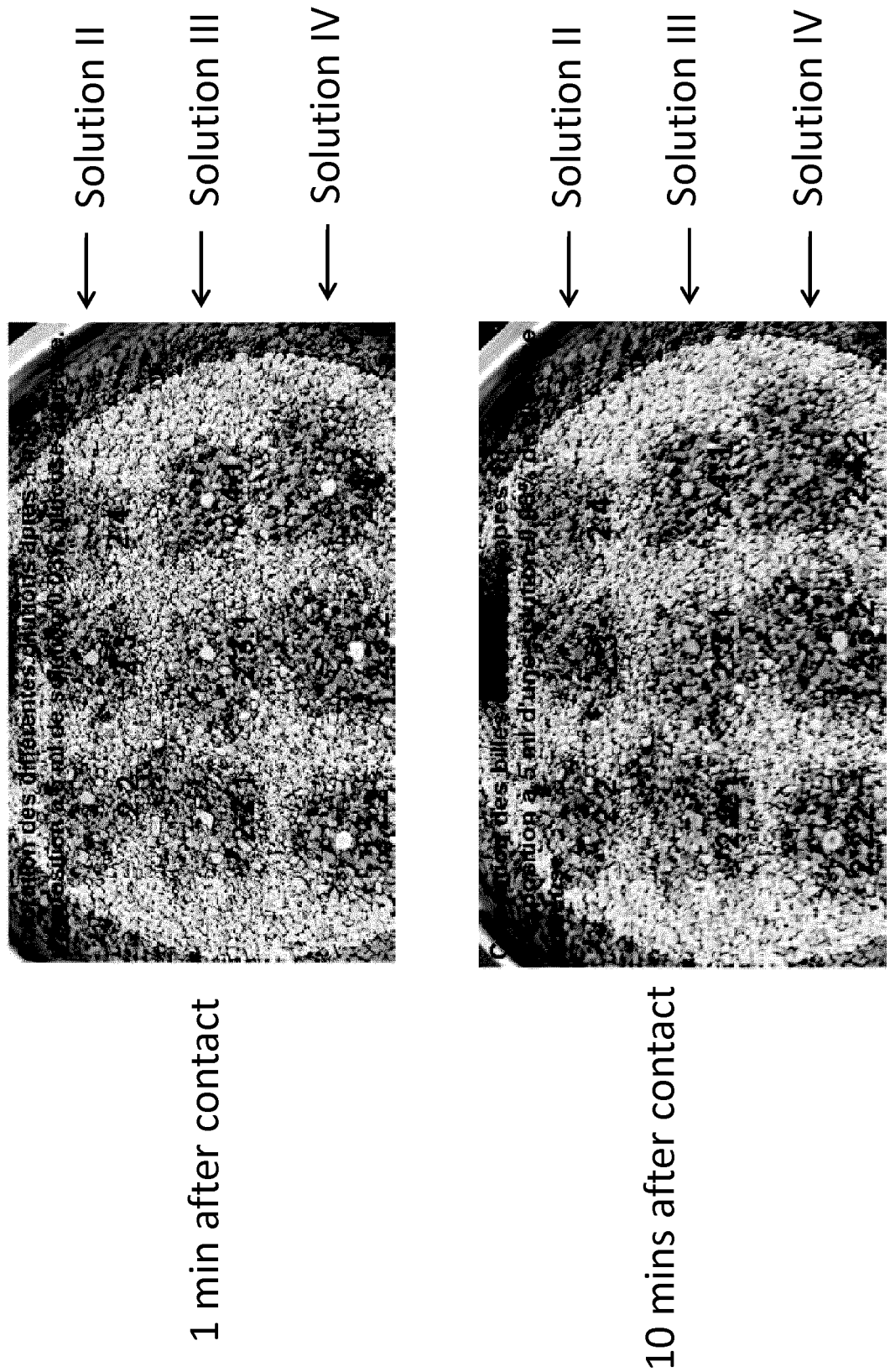
FIG. 5 shows photographs of samples of particles of chromogenic absorbent materials including after 1 minute and 10 minutes of contact with glucose solutions of different concentrations.

FIG. 5 shows particles of chromogenic absorbent material 1 minute (top picture) and 10 minutes (bottom picture) after contact with a solution containing 0.03% of glucose. In each picture, the top row corresponds to chromogenic absorbent material made with chromogenic solution II, the middle row corresponds to chromogenic absorbent material made with chromogenic solution III, and the bottom row corresponds to chromogenic absorbent material made with chromogenic solution IV. As can be seen, when the more concentrated solution II was used, the blue coloration is deeper and appears within 1 minute of contact. When the lower concentration solution IV is used, the deep blue coloration appeared within 10 minutes of contact.

Experimentation Series 4

Experiments were also performed by measuring the free swelling capacity (FSC) of particles of chromogenic absorbent material. The particles of chromogenic absorbent material were prepared as described in Example 1 using PGS, Xanthan or guar as the water-absorbing polysaccharide, and MCC. The measurements were performed by soaking the samples in water for 30 minutes and draining the water remaining at the surface for 10 minutes. The values obtained were compared with the FSC values of particles obtained by extrusion or pressing. The results are detailed in Table 5.

TABLE 5

| Particle type | FSC % |
|---|---|
| Extruded starch granule without gas injection (comparative) | 190 |
| Extruded starch granule with gas injection (comparative) | 200 |
| Pressed paper pulp pellet (comparative) | 500 |
| 50% PGS/50% MCC granule (sample No. 25 of Example 2) | 1080 |
| 50% Xanthan/50% MCC granule | 3360 |
| 50% guar gum/50% MCC granule | 2030 |

The particles of chromogenic absorbent material made from PGS/MCC, xanthan/MCC and guar gum/MCC all exhibit high FSC values. This is indicative of a very high porosity and surprisingly high absorption properties when compared with the extruded starch granules and pressed paper pulp pellets known in the art.

Experimentation Series 5

Experiments have also been performed by measuring the density of particles of chromogenic absorbent material. The particles of chromogenic absorbent material were prepared as described in Example 1 using PGS, Xanthan or guar as the water-absorbing polysaccharide, and MCC. The values obtained were compared with the density values of particles known in the art and obtained by extrusion or pressing. The results are detailed in Table 6.

TABLE 6

| Particle type | Density (g/cm$^3$) |
|---|---|
| Extruded starch granule without gas injection (comparative) | 0.60 |
| Extruded starch granule with gas injection (comparative) | 0.48 |
| Pressed paper pulp pellet (comparative) | 0.40 |
| 50% PGS/50% MCC granule (sample No. 25 of Example 2) | 0.33 |
| 50% Xanthan/50% MCC granule | 0.37 |
| 50% guar gum/50% MCC granule | 0.26 |

The particles of chromogenic absorbent material made from PGS/MCC, xanthan/MCC and guar gum/MCC exhibit lower density values when compared with the extruded starch granules and pressed paper pulp pellets known in the art.

Experimentation Series 6

Experiments have been performed to obtain scanning electron micrographs of cross sections of particles of extruded starch with or without injected gas during extrusion (FIGS. 7A and 7B, comparative) and of a cross section of a particle of chromogenic absorbent material corresponding to sample 25 as shown in Example 2 (FIG. 7C). The images obtained were analyzed to determine the pore density and the equivalent diameter of the pores. Prior to imaging, the respective particles were first hardened by freezing in liquid nitrogen and cut in the frozen state. The scanning electron microscope used was a MEB JEOL JSM-5900LV™ (low vacuum).

The pore density and equivalent diameter measurements were performed by using the Nikon NIS-Elements D™ image analysis software. The results are detailed in Table 7.

TABLE 7

| Particle type | Pore density (%) | Equivalent diameter (μm) |
|---|---|---|
| Extruded starch granule without gas injection (comparative) | 7.6 | 7.8 |
| Extruded starch granule with gas injection (comparative) | 10.8 | 11.5 |
| 50% PGS/50% MCC granule (sample No. 25 of Example 2) | 29.5 | 25.3 |

The particles of corresponding to sample No. 25 of Example 2 have a higher pore density and equivalent pore diameter than the particles of extruded starch (made with or without gas injection during high shear extrusion).

Experimentation Series 7

Experiments have been performed on sample No. 25 of Example 2 to measure the total porosity and effective porosity of particles of chromogenic absorbent material. Comparative measurements were also performed on extruded starch granules (with or without injected gas during high shear extrusion). The porosity measurements were performed as follows.

200 mL of particles were placed in a container. The particles were weighed (mass m). Acetone was added to soak the particles and completely cover the particles with solvent. The volume of solvent required to cover all the particles was measured (Vc). The soaked particles were removed from the container and the volume of remaining solvent was measured (Vr). The volume of liquid absorbed by the chromogenic absorbent particles (Va=Vc−Vr) was calculated. The total porosity is then obtained by calculating the ratio of the volume of added liquid (Vc) to the volume of particles (V), and the effective porosity is calculated using Equation 2 detailed above. The results are summarized in Table 8.

TABLE 8

| Particle type | Mass of particles (g) | Vc (mL) | Va (mL) | Total porosity (%) | Effective porosity (mL/g) |
|---|---|---|---|---|---|
| Extruded starch granule without gas injection (comparative) | 120 | 104 | 18 | 52% | 0.15 |
| Extruded starch granule with gas injection (comparative) | 96 | 116 | 16 | 58% | 0.167 |
| 50% PGS/50% MCC granule (sample No. 25 of Example 2) | 66 | 150 | 65 | 75% | 0.985 |

As can be seen, the particles of chromogenic absorbent material made of 50% PGS and 50% MCC have an effective porosity which is substantially higher than extruded starch particles obtained with or without gas injection during high shear extrusion.

Experimentation Series 8

Experiments were performed by preparing particles of chromogenic absorbent material (i.e. particles of water-absorbing material) using an absorptive powder mixture having the following composition: 49 wt % PGS; 49% MCC; and 2 wt % sodium polyacrylate (SAP).

The particles were prepared using a Bogen universal indicator solution detailed in table 9 below:

TABLE 9

| Components of the chromogenic solution (pH Indicator solution) | wt % |
| --- | --- |
| Water | 52.4 |
| Ethanol | 43 |
| 2-propanol | 2.4 |
| Methanol | 2.1 |
| Bromothymol blue (sodium salt) | 0.06 |
| Phenolphthalein | 0.06 |
| Methyl red | 0.02 |

Particles of chromogenic absorbent material were prepared by mixing pregelatinized starch (PGS), microcrystalline cellulose (MCC) and sodium polyacrylate as the superabsorbent polymer (SAP), in powder form, thereby obtaining the absorptive powder mixture; The absorptive powder mixture was disposed onto a laboratory bench top to obtain a powder bed; the chromogenic solution was dripped onto the powder bed to obtain solution-impregnated humid particles; the solution-impregnated humid particles were maintained immobile on the bench top (i.e. in substantially shear-less conditions) for several seconds until the solution-impregnated humid particles agglomerated into stable agglomerated humid particles; and agglomerated humid particles were dried in an oven at 65° C. to obtain the particles of chromogenic absorbent material. In this case, the particles of chromogenic absorbent material were obtained in the form of granules having a length of between about 0.25 cm and about 0.75 cm.

The particles were tested to measure the pH of various pH-controlled solutions, and the results are summarized in Table 10 below:

TABLE 10

| pH | Color |
| --- | --- |
| 4 | Red |
| 5 | Orange |
| 6 | Orange-yellow |
| 7 | Yellow-green |
| 8 | Green |
| 9 | Blue-green |
| 10 | Blue |

Experimentation Series 9

Experiments were performed by preparing particles of chromogenic absorbent material (i.e. particles of water-absorbing material) having the compositions shown in Table 11, and using the process described in Example 1 and the chromogenic solution shown in Table 1.

TABLE 11

| No. | wt % MCC | wt % PGS | wt % SAP |
| --- | --- | --- | --- |
| 9.1 | 50 | 50 | 0 |
| 9.2 | 49 | 49 | 2 |
| 9.3 | 39 | 59 | 2 |
| 9.4 | 59 | 39 | 2 |
| 9.5 | 49 | 49 | 2 |

It is also noted that particles 9.5 and particles 9.2 have the same composition, but particles 9.5 have been further dried under vacuum after having been heat-dried. Particles 9.1 to 9.5 have a spheroidal shape. The hardness of particles 9.1 to 9.5 has been measured by applying axial and lateral compression forces such that the particles are compressed by 1 mm. The compression speed was of 10 mm/min from 0 mm of compression to 1.1 mm of compression. It is noteworthy that an "axial" compression corresponds to a compression in an axis coaxial to the axis of the dripping, and that a "lateral" is a compression in an axis perpendicular to the axis of the dripping.

The force necessary to compress the particles by 1 mm is shown in Table 12. The particles were also compressed by 1.1 mm and the % of particles which broke or were disaggregated is also shown in Table 12.

TABLE 12

| No. | Type of compression force | Force at 1 mm compression (N) | Mean weight of the particles (mg) | % of particles which break after 1.1 mm compression |
| --- | --- | --- | --- | --- |
| 9.1 | axial | 57 ± 10 | 27.5 | 20% |
| 9.2 | axial | 74 ± 15 | 26.1 | 0% |
| 9.3 | axial | 82 ± 11 | 23.8 | 0% |
| 9.4 | axial | 26 ± 5 | 23.0 | 20% |
| 9.5 | axial | 84 ± 17 | 36.2 | 0% |
| 9.1 | Lateral | 25 ± 4 | 23.7 | 0% |
| 9.2 | Lateral | 25 ± 6 | 28.5 | 0% |
| 9.3 | Lateral | 38 ± 5 | 25.5 | 0% |
| 9.4 | Lateral | 14 ± 1 | 25.6 | 0% |
| 9.5 | Lateral | 35 ± 5 | 35.6 | 0% |

Experimentation Series 10

Experiments were performed to assess the physical behavior of chromogenic particles when mixed with an animal litter. 1.5 g of Chromogenic particles 25 (described in Example 2) were mixed with a bed of animal litter particles provided in a container. The bed of animal litter particles had a thickness of about 1.5 inches. The mixing was performed such that the chromogenic particles were evenly distributed within the animal litter. The container was then shaken laterally to verify whether the chromogenic particles migrated to the surface of the bed of animal litter particles. Various types of animal litter were tested separately, including animal litter based on the following components:
bentonite;
montmorillonite;
attapulgite;
fine silica beads (Nullodor™);
coarse silica with blue crystals (President's Choice™);
ECO LIFE™; and
a paper-based litter (Daily Scoops™).

In all cases, the chromogenic particles 25 migrated to the surface.

When water was added to the animal litter, the chromogenic particles 25 expanded after absorbing the water, and still migrated to the surface of the animal litter.

Experimentation Series 11

Experiments were performed by preparing particles of chromogenic absorbent material (i.e. particles of water-absorbing material) using the chromogenic solution V shown in Table 13, and testing the particles when contacted with a blood-containing solution.

Particles of chromogenic absorbent material were prepared by mixing PGS (49 wt %), MCC (49 wt %) and sodium polyacrylate (2 wt %), in powder form, thereby obtaining an absorptive powder mixture; The absorptive powder mixture was disposed onto a laboratory bench top to obtain a powder bed; the chromogenic solution was dripped onto the powder bed to obtain solution-impregnated humid particles; the solution-impregnated humid particles were maintained immobile on the bench top (i.e. in substantially shear-less conditions) for several seconds until the solution-impregnated humid particles agglomerated into stable agglomerated humid particles; and agglomerated humid particles were dried in an oven at 65° C. to obtain the particles of chromogenic absorbent material. In this case, the particles of chromogenic absorbent material were obtained in the form of granules having a length of between about 0.25 cm and about 0.75 cm. The granules were formed by dripping the solution V on the absorptive powder mixture with a solution:powder ratio of 1:1 (v/w).

The chromogenic solution V that was used is detailed in Table 13:

TABLE 13

| Compound | % w/w |
|---|---|
| Water (solvent) | 54.86 |
| Acetone (solvent) | 43.89 |
| TMB (chromogenic indicator) | 0.34 |
| CHP (oxidizing agent) | 0.43 |
| 4-lepidine (color enhancer) | 0.24 |
| 6-Methoxyquinoline (stabilizer) | 0.17 |
| EDTA (free acid 0.5M - metal scavenger agent) | 0.06 |
| BHT (stabilizer) | 0.01 |

The chromogenic absorbent particles made with chromogenic solution V were used for detecting traces of blood in excretions having a pH of 8 or greater and/or containing proteins.

Experimentation Series 12

Experiments were performed by preparing particles of chromogenic absorbent material (i.e., particles of water-absorbing material) using an absorptive powder mixture having the following composition: 49 wt % PGS; 49% MCC; and 2 wt % sodium polyacrylate (SAP), and using the chromogenic solution V shown in Table 13. The following additional steps were then performed:

the particles of chromogenic absorbent material were ground to obtain a ground absorbent material; and the ground absorbent material was successively sieved over 12, 20, 60 and 100 mesh sieves and particles of various sizes were separated.

0.1 g of absorbent material was placed in a cupule for each particle size of sieved absorbent material (<100 mesh, 60-100 mesh, 20-60 mesh, 12-20 mesh and >12 mesh), and 3 drops of an aqueous solution containing blood (30 rbc/µL-rbc=red blood cell) was dripped onto the absorbent material. The coloration of each sample was monitored as a function of time. The results are summarized in Table 14 below.

TABLE 14

| Time | >12 mesh | 12-20 mesh | 20-60 mesh | 60-100 mesh | <100 mesh |
|---|---|---|---|---|---|
| t = 0 | 0 | 0 | 0 | 0 | 0 |
| t = 1 min | 2+ | 2+ | 2+ | 2+ | 2+ |
| t = 6 mins | 3+ | 3+ | 3+ | 3+ | 3+ |
| t = 18 mins | 3+ | 3+ | 3+ | 3+ | 3+ |
| t = 4 h | 3+ | 3+ | 3+ | 2+ | 2+ |
| t = 3 days | 2+ | 2+ | 1+ | 0-1+ | 0-1+ |

* Color scale used: 0 corresponds to white; 1+ corresponds to a light blue color (e.g. Pantone code 7457 or similar); 2+ corresponds to a blue color (e.g. Pantone codes 369U-630U or similar); and 3+ corresponds to a dark blue color (e.g. Pantone codes 631U-634U or similar).

All of the particle sizes were shown to exhibit a strong coloration within a few minutes of exposure to traces of blood. It was also shown that the absorbent material which was sieved through sieves of 20 mesh and 12 mesh exhibited a more intense coloration which lasted longer than the more finely sieved absorbent material.

Experimentation Series 13

Experiments were performed by incorporating the sieved absorbent material of Example 12 into puppy pads (for each particle size of sieved absorbent material). Puppy pads of the brand Hartz™ were used. For each particle size, a surface of 4.8 cm by 9.5 cm was cut. The first non-woven layer and the first paper layer of the puppy pads were removed, and 0.1 g of sieved absorbent material was evenly sprinkled on the puppy pads. The two removed layers were put back in place, over the sprinkled absorbent material. 15 drops of an aqueous solution containing blood (30 rbc/µL) were dripped onto the absorbent material. The coloration of each surface of puppy pad was monitored as a function of time. The results are summarized in Table 15 below (same color scale as Table 14).

TABLE 15

| Time | >12 mesh | 12-20 mesh | 20-60 mesh | 60-100 mesh | <100 mesh |
|---|---|---|---|---|---|
| t = 0 | 0 | 0 | 0 | 0 | 0 |
| t = 1 min | 0-1+ | 0-1+ | 0 | 0 | 0 |
| t = 5 mins | 1-2+ | 1-2+ | 1+ | 0-1+ | 0-1+ |
| t = 15 mins | 3+ | 2-3+ | 1+ | 0-1+ | 0-1+ |
| t = 1 h | 3+ | 3+ | 2+ | 1+ | 1+ |
| t = 3 days | 0-1+ | 0-1+ | 0 | 0 | 0 |

The coloration of the particle was visible through the first layers of the puppy pads for all particle sizes. The coloration was more diffuse/less intense for the smaller particle sizes (60-100 mesh and <100 mesh) but it was not possible to detect the presence of the particles through the layers by touch. The coloration was more intense for the larger particle sizes (>12 mesh and 12-20 mesh) but it was possible to detect the presence of the particles through the layers by touch. It was evaluated that the use of particles of sizes between 20 and 60 mesh was a compromise between coloration intensity and being able to feel the particles through the layers (feeling the particles through the layers could be a deterrent to puppies using the puppy pad).

Experimentation Series 14

Experiments were performed by incorporating the sieved absorbent material of Example 12 into puppy pads (for each particle size of sieved absorbent material), as in Example 13.

Puppy pads of the brand Hartz™ were used. For each particle size, a surface of 4.8 cm by 9.5 cm was cut. The first non-woven layer and the first paper layer of the puppy pads were removed, and varying amounts of sieved absorbent material were evenly sprinkled on the puppy pads (0.075 g, 0.05 g and 0.025 g). The two removed layers were put back in place, over the sprinkled absorbent material. 15 drops of an aqueous solution containing blood (30 rbc/μL) were dripped onto the absorbent material. The coloration of each surface of puppy pad was monitored as a function of time for two particle sizes (12-20 mesh and 20-60 mesh). The results are summarized in Table 16 below (same color scale as Table 14).

TABLE 16

| Time | 12-20 mesh; 0.025 g of material | 20-60 mesh; 0.025 g of material | 12-20 mesh; 0.05 g of material | 20-60 mesh; 0.05 g of material | 12-20 mesh; 0.075 g of material | 20-60 mesh; 0.075 g of material |
|---|---|---|---|---|---|---|
| t = 0 | 0 | 0 | 0 | 0 | 0 | 0 |
| t = 5 min | 0-1+ | 0-1+ | 1+ | 1+ | 2+ | 2+ |
| t = 1 h 20 | 1+ | 1+ | 1+ | 1+ | 2+ | 2+ |
| t = 3 h | 1+ | 1+ | 2+ | 2+ | 3+ | 3+ |
| t = 3 days | 0 | 0 | 0 | 0 | 1+ | 1+ |

It was determined that the minimal quantity of absorbent material to sprinkle onto a puppy pad of the brand Hartz™ was of about 5 g of sprinkled absorbent material (having a particle size between 20-60 mesh) per square meter of puppy pad, in order to perceive the coloration through the layers up to several hours after contacting excretion.

Similar tests were performed using puppy pads of the brand Out!™. It was shown that the minimal quantity of absorbent material to sprinkle onto a puppy pad of the brand Out!™ was also of about 5 g of sprinkled absorbent material (having a particle size between 20-60 mesh) per square meter of puppy pad, in order to perceive the coloration through the layers up to several hours after contacting excretion.

Experimentation Series 15

Experiments were performed by preparing particles of absorbent material (i.e., particles of water-absorbing material) using an absorptive powder mixture having the following composition: 49 wt % PGS; 49% MCC; and 2 wt % sodium polyacrylate (SAP), and using a water-acetone solution (50/50) in order to form solution-impregnated humid material. In this Example, the particles of absorbent material did not initially include a chromogenic indicator. The particles of absorbent material were then ground and sieved as in Example 12, and the sieved material obtained was introduced below the first non-woven layer of a puppy pad (the brand used was Hartz™). An aqueous solution including blood (30 rbc/μL) was dripped onto the puppy pad, and chromogenic solution V of Table 13 was then vaporised onto the puppy pad. The results were compared to entries of Table 14.

It was observed that the coloration generally appeared more quickly when the chromogenic solution was vaporised onto the absorbent material than when the absorbent material was initially impregnated with the chromogenic solution. It was also observed that the coloration was visible for a longer time period when the absorbent material was initially impregnated with the chromogenic solution than when the chromogenic solution was vaporised onto the absorbent material.

Experimentation Series 16

Experiments were performed by preparing particles of chromogenic absorbent material for detecting proteins. The particles of chromogenic absorbent material were prepared by dripping a buffer solution onto a bed of water-absorbing material. The compositions of the water-absorbing material and the buffer solution are shown in Tables 17 and 18, respectively. The wetted granules thereby obtained were dried in an oven at 65° C. for 120 minutes to obtain pale yellow particles of chromogenic absorbent material.

The particles of chromogenic absorbent material were contacted with two drops of solutions containing various concentrations of egg albumin (0, 30, 100 and 500 mg/dl) in demineralized water.

TABLE 17 composition of the water-absorbing material

| Compound | Molar mass (g/mol) | Mass or volume | wt % |
|---|---|---|---|
| Citric acid | 192.12 | 210 mg | 4.2 |
| Sodium citrate | 258.06 | 46 mg | 0.9 |
| Tetrabromophenol blue | 669.95 | 50 mg | 1.0 |
| MCC | — | 2.30 g | 46 |
| PGS | — | 2.30 g | 46 |
| SAP | — | 94 mg | 1.9 |

TABLE 18 composition of the buffer solution

| Compound | Volume (mL) | pH |
|---|---|---|
| Citric acid 0.1M | 20.5 | 2.99 |
| Sodium citrate 0.1M | 4.5 | |

A blue coloration appeared two seconds after contacting the albumin solution with the particles of chromogenic absorbent material (for the solutions having a concentration of 30, 100 and 500 mg/dl). A more intense coloration was observed for the more concentrated samples tested. No coloration was observed after contacting the particles of chromogenic absorbent material with the solution having an egg albumin concentration of 0 mg/dl.

Experimentation Series 16

Experiments were performed by preparing particles of chromogenic absorbent material for detecting ketone bodies. The particles of chromogenic absorbent material were prepared by dripping a chromogenic solution onto a bed of water-absorbing material. The chromogenic solution was prepared by adding the components while mixing. The compositions of the chromogenic solution and the water-absorbing material are shown in Tables 19 and 20, respectively. The wetted granules thereby obtained were dried in an oven at 65° C. for 120 minutes to obtain white particles of chromogenic absorbent material.

The particles of chromogenic absorbent material were contacted with two drops of solutions containing various concentrations of acetone (0, 0.5, 1.0 and 2.0 g/dl) in demineralized water.

TABLE 19 composition of the chromogenic solution

| Compound | Molar mass (g/mol) | Mass or volume | Concentration (mol/L) |
|---|---|---|---|
| Water | — | 50 mL | |
| Tris(hydroxymethyl)amino methane (TRIS) $NH_2C(CH_2OH)_3$ | 121.14 | 12.11 g | 2.0 |
| Magnesium sulphate heptahydrate $MgSO_4 \cdot 7H_2O$ | 246.47 | 27.5 g | 2.2 |
| Aminomethanesulfonic acid (AMSA) $NH_2CH_2SO_3H$ | 111.12 | 9.25 g | 1.7 |
| Sodium nitroprusside dihydrate | 297.95 | 2.8 | 0.2 |

TABLE 20 composition of the water-absorbing material

| Compound | wt % |
|---|---|
| MCC | 49 |
| PGS | 49 |
| SAP | 2 |

A purple coloration gradually appeared within minutes after contacting the acetone solution with the particles of chromogenic absorbent material (for the solutions having a concentration of 0.5, 1.0 and 2.0 g/dl). A more intense coloration was observed for the more concentrated samples tested. No coloration was observed after contacting the particles of chromogenic absorbent material with the solution having a ketone concentration of 0 mg/dl.

The invention claimed is:

1. A process for manufacturing a chromogenic absorbent material for detecting blood, comprising:
   providing an absorptive powder onto a surface, thereby obtaining a powder bed, the absorptive powder comprising:
      between about 35 wt % and 65 wt % of a water-absorbing polysaccharide, the water-absorbing polysaccharide being a glass-like polysaccharide; and
      between about 35 wt % and 65 wt % of a crystalline polysaccharide, the crystalline polysaccharide being less water-absorbent than the water-absorbing polysaccharide;
   releasing a chromogenic aqueous solution as discrete drops onto the powder bed to form a solution-impregnated humid material, the chromogenic aqueous solution comprising:
      an oxidizing agent responsive to peroxidatic/pseudoperoxidatic activity; and
      a chromogenic indicator oxidizable into a colored and/or fluorescent substance in the presence of the oxidizing agent and blood;
   maintaining the solution-impregnated humid material supported by the surface in substantially shear-less conditions, until the solution-impregnated humid material agglomerates to form agglomerated humid particles;
   drying the agglomerated humid particles, thereby obtaining dried agglomerated particles; and
   reducing a particle size of the dried agglomerated particles by grinding and/or sieving.

2. The process of claim 1, wherein the glass-like polysaccharide comprises pregelatinized starch.

3. The process of claim 1, wherein the crystalline polysaccharide comprises microcrystalline cellulose (MCC), nanocrystalline cellulose (NCC) or a mixture thereof.

4. The process of claim 1, wherein the absorptive powder further comprises up to about 3 wt % of a superabsorbent polymer (SAP).

5. The process of claim 4, wherein the SAP comprises a poly(acrylic acid), a poly(methacrylic acid), a salt thereof, or a mixture thereof.

6. The process of claim 4, wherein the SAP comprises sodium polyacrylate.

7. The process of claim 1, wherein the oxidizing agent is a hydroperoxide or a hydroperoxide precursor.

8. The process of claim 1, wherein the chromogenic indicator comprises a benzidine-type compound.

9. The process of claim 1, wherein reducing the particle size of the dried agglomerated particles comprises:
   grinding the dried agglomerated particles to obtain a ground agglomerated material; and
   sieving the ground agglomerated material to obtain a sieved agglomerated material.

10. The process of claim 9, wherein the sieved agglomerated material has a particle size between 100 mesh and 12 mesh.

11. The process of claim 9, wherein the sieved agglomerated material has a particle size between 60 mesh and 8 mesh.

12. The process of claim 9, wherein the grinding is performed using at least one of a belt grinder, a bench grinder, a cylindrical grinder, a surface grinder, a tool grinder, a jig grinder, a gear grinder and a die grinder.

13. The process of claim 9, further comprising incorporating the sieved agglomerated material into a diaper or a puppy pad.

14. The process of claim 13, wherein the sieved agglomerated material is incorporated between layers of the diaper or the puppy pad.

15. The process of claim 1, wherein the surface is substantially planar.

16. The process of claim 1, wherein the surface extends substantially horizontally.

17. The process of claim 1, wherein the chromogenic aqueous solution is released from a solution dispenser disposed above the surface, the process further comprising displacing the solution-impregnated humid material away from the solution dispenser.

18. The process of claim 17, wherein the powder bed is in translation relative to the solution dispenser.

19. The process of claim 1, further comprising controlling a thickness of the powder bed between about 1 cm and about 5 cm.

20. The process of claim 1, wherein the drying comprises at least one of drying under vacuum and drying by heating.

* * * * *